(12) United States Patent
Ramsey et al.

(10) Patent No.: US 10,571,428 B2
(45) Date of Patent: *Feb. 25, 2020

(54) NANOFLUIDIC DEVICES FOR THE RAPID MAPPING OF WHOLE GENOMES AND RELATED SYSTEMS AND METHODS OF ANALYSIS

(71) Applicant: The University of North Carolina at Chapel Hill, Chapel Hill, NC (US)

(72) Inventors: John Michael Ramsey, Chapel Hill, NC (US); Laurent Menard, Raleigh, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 36 days.

This patent is subject to a terminal disclaimer.

(21) Appl. No.: 15/949,178

(22) Filed: Apr. 10, 2018

(65) Prior Publication Data

US 2018/0224398 A1 Aug. 9, 2018

Related U.S. Application Data

(62) Division of application No. 14/771,989, filed as application No. PCT/US2014/023371 on Mar. 11, 2014, now Pat. No. 9,970,898.

(Continued)

(51) Int. Cl.
*G01N 33/487* (2006.01)
*G01N 27/447* (2006.01)
(Continued)

(52) U.S. Cl.
CPC .. *G01N 27/44791* (2013.01); *B01L 3/502715* (2013.01); *B01L 3/502761* (2013.01);
(Continued)

(58) Field of Classification Search
CPC ..... B01L 2300/0896; B01L 2400/0421; B01L 3/502715; B01L 2300/0645;
(Continued)

(56) References Cited

U.S. PATENT DOCUMENTS 5,498,392 A 3/1996 Wilding et al.
5,858,187 A 1/1999 Ramsey et al.
(Continued)

FOREIGN PATENT DOCUMENTS

JP 2003-166934 6/2003
JP 2005-102619 4/2005
(Continued)

OTHER PUBLICATIONS

Abgrall et al. "Nanofluidic Devices and Their Applications" *Analytical Chemistry* 80:2326-2341 (2008).
(Continued)

*Primary Examiner* — Betty J Forman
(74) *Attorney, Agent, or Firm* — Myers Bigel, P.A.

(57) ABSTRACT

Devices and methods generate an ordered restriction map of genomic DNA extracted from whole cells, nuclei, whole chromosomes, or other sources of long DNA molecules. The devices have a fluidic microchannel that merges into a reaction nanochannel that merges into a detection nanochannel at an interface where the nanochannel diameter decreases in size by between 50% to 99%. Intact molecules of DNA are transported to the reaction nanochannel and then fragmented in the reaction nanochannel using restriction endonuclease enzymes. The reaction nanochannel is sized and configured so that the fragments stay in an original order until they are injected into the detection nanochannel. Signal at one or more locations along the detection nanochannel is detected to map fragments in the order they occur along a long DNA molecule.

13 Claims, 21 Drawing Sheets

Related U.S. Application Data

(60) Provisional application No. 61/778,746, filed on Mar. 13, 2013.

(51) Int. Cl.
  *C12Q 1/683* (2018.01)
  *B01L 3/00* (2006.01)
  *C12Q 1/6869* (2018.01)

(52) U.S. Cl.
  CPC ........... *C12Q 1/683* (2013.01); *C12Q 1/6869* (2013.01); *G01N 33/48721* (2013.01); *B01L 2300/0896* (2013.01); *B01L 2400/0418* (2013.01); *B01L 2400/0421* (2013.01)

(58) Field of Classification Search
  CPC ..... B01L 2400/0418; B01L 2300/0867; B01L 3/502761; B01L 3/5027; G01N 33/48721; G01N 27/44791; B81B 1/006; B81B 2201/058; B81B 2203/0323; B81C 2201/034; C08G 18/5015; C08G 18/8116; C08G 2650/48; C08G 65/007; C08G 65/33348; C12Q 1/6816; C12Q 2565/629; C12Q 1/683; C12Q 2561/113
  See application file for complete search history.

(56) References Cited

U.S. PATENT DOCUMENTS

| | | | |
|---|---|---|---|
| 5,872,010 | A | 2/1999 | Karger et al. |
| 6,235,471 | B1 | 5/2001 | Knapp et al. |
| 6,524,456 | B1 | 2/2003 | Ramsey et al. |
| 6,790,671 | B1 | 9/2004 | Austin et al. |
| 6,803,568 | B2 | 10/2004 | Bousse et al. |
| 7,033,474 | B1 | 4/2006 | Dubrow et al. |
| 7,465,381 | B2 | 12/2008 | Lopez et al. |
| 7,670,770 | B2 | 3/2010 | Chou et al. |
| 7,744,762 | B2 | 6/2010 | Lazar |
| 7,960,105 | B2 | 6/2011 | Schwartz et al. |
| 8,246,799 | B2 | 8/2012 | Oliver et al. |
| 8,333,934 | B2 | 12/2012 | Cao et al. |
| 8,691,588 | B2 | 4/2014 | Park et al. |
| 8,722,327 | B2 | 5/2014 | Cao et al. |
| 8,735,065 | B2 | 5/2014 | Craighead et al. |
| 8,764,968 | B2 | 7/2014 | Afzali-Ardakani et al. |
| 9,061,901 | B2 | 6/2015 | Cao et al. |
| 9,255,288 | B2 | 2/2016 | Ramsey et al. |
| 9,618,479 | B2 | 4/2017 | Ramsey et al. |
| 2002/0000516 | A1 | 1/2002 | Schultz et al. |
| 2002/0061529 | A1 | 5/2002 | Bridgham et al. |
| 2002/0072243 | A1 | 6/2002 | Craighead et al. |
| 2002/0081744 | A1 | 6/2002 | Chan et al. |
| 2002/0160365 | A1 | 10/2002 | O'Brien |
| 2002/0190204 | A1 | 12/2002 | Hofstadler et al. |
| 2002/0197603 | A1 | 12/2002 | Chow et al. |
| 2003/0146377 | A1 | 8/2003 | Miller et al. |
| 2004/0033515 | A1 | 2/2004 | Cao et al. |
| 2004/0166504 | A1 | 8/2004 | Rossier et al. |
| 2005/0023156 | A1 | 2/2005 | Ramsey et al. |
| 2005/0082204 | A1 | 4/2005 | Schwartz et al. |
| 2005/0103713 | A1 | 5/2005 | Ramsey et al. |
| 2005/0196746 | A1 | 9/2005 | Xu et al. |
| 2006/0084078 | A1 | 4/2006 | Zhao |
| 2006/0169587 | A1 | 8/2006 | Lopez et al. |
| 2006/0240573 | A1 | 10/2006 | Kao et al. |
| 2006/0275778 | A1 | 12/2006 | Wu et al. |
| 2006/0278879 | A1 | 12/2006 | Busta |
| 2007/0057179 | A1 | 3/2007 | Bousse et al. |
| 2007/0145263 | A1 | 6/2007 | Weng |
| 2007/0192911 | A1 | 8/2007 | Jin et al. |
| 2008/0057192 | A1 | 3/2008 | Faguet |
| 2009/0023146 | A1 | 1/2009 | Harnack et al. |
| 2009/0111115 | A1 | 4/2009 | Drmanac et al. |
| 2009/0115094 | A1 | 5/2009 | Chou et al. |
| 2009/0136682 | A1 | 5/2009 | Branton et al. |
| 2009/0305273 | A1 | 12/2009 | Cao et al. |
| 2010/0029508 | A1 | 2/2010 | Austin et al. |
| 2010/0075428 | A1 | 3/2010 | Wang et al. |
| 2010/0159462 | A1 | 6/2010 | Takayama et al. |
| 2010/0267158 | A1 | 10/2010 | Chou et al. |
| 2011/0036994 | A1 | 2/2011 | Frayling |
| 2011/0155575 | A1 | 6/2011 | Dorairaj et al. |
| 2011/0201509 | A1 | 8/2011 | Tegenfeldt et al. |
| 2011/0226623 | A1 | 9/2011 | Timp et al. |
| 2011/0227558 | A1 | 9/2011 | Mannion et al. |
| 2011/0296903 | A1 | 12/2011 | Cao et al. |
| 2011/0308949 | A1 | 12/2011 | Afzali-Ardakani et al. |
| 2012/0193231 | A1 | 8/2012 | Afzali-Ardakani et al. |
| 2012/0196376 | A1 | 8/2012 | Park et al. |
| 2013/0068618 | A1 | 3/2013 | Harrer et al. |
| 2013/0195723 | A1 | 8/2013 | Ramsey et al. |
| 2013/0224736 | A1 | 8/2013 | Marie et al. |
| 2013/0224763 | A1 | 8/2013 | Kimura |
| 2013/0341190 | A1 | 12/2013 | Quake et al. |
| 2014/0194313 | A1 | 7/2014 | Craighead et al. |
| 2014/0194314 | A1 | 7/2014 | Walsworth et al. |
| 2014/0197105 | A1 | 7/2014 | DiBiasio et al. |
| 2014/0238856 | A1 | 8/2014 | Ramsey et al. |
| 2014/0272958 | A1 | 9/2014 | Ramsey et al. |
| 2015/0008124 | A1 | 1/2015 | Oliver |
| 2016/0024569 | A1 | 1/2016 | Ramsey et al. |
| 2017/0175181 | A1 | 6/2017 | Ramsey et al. |

FOREIGN PATENT DOCUMENTS

| | | |
|---|---|---|
| JP | 2007-149861 | 6/2007 |
| WO | WO 96/04547 A1 | 2/1996 |
| WO | WO 00/002038 A1 | 1/2000 |
| WO | WO 01/13088 A1 | 2/2001 |
| WO | WO 03/025540 A2 | 3/2003 |
| WO | WO 2007/011622 A2 | 1/2007 |
| WO | WO 2008/079169 A2 | 7/2008 |
| WO | WO 2008/132734 A2 | 11/2008 |
| WO | WO 2009/030953 A1 | 3/2009 |
| WO | WO 2009/052214 A2 | 4/2009 |
| WO | WO 2009/120642 A1 | 10/2009 |
| WO | WO 2012/040098 A2 | 3/2012 |
| WO | WO 2012/055415 A1 | 5/2012 |
| WO | WO 2012/170560 A2 | 12/2012 |
| WO | WO 2013/039778 A2 | 3/2013 |
| WO | WO 2013/088098 A2 | 6/2013 |
| WO | WO 2013/119765 A1 | 8/2013 |
| WO | WO 2013/176767 A1 | 11/2013 |
| WO | WO 2013/191908 A1 | 12/2013 |

OTHER PUBLICATIONS

Ai et al. "Field Effect Regulation of DNA Translocation through a Nanopore" *Analytical Chemistry* 82(19):8217-8225 (2010).

Alkan et al. "Genome structural variation discovery and genotyping" *Nat. Rev. Genet.* 12:363-376 (2011).

Allison et al. "Direct atomic force microscope imaging of EcoRI endonuclease site specifically bound to plasmid DNA molecules" *Proc. Natl. Acad. Sci. USA*, 93:8826-8829 (1996).

Apel et al. "Diode-like single-ion track membrane prepared by electro☐stopping" *Nucl. Instrum. Methods Phys. Res.*, Sect. B, 2001, 184, 337-346.

Baday et al., "Multicolor super-resolution DNA imaging for genetic analysis", *Nano Lett.*, 2012, vol. 12, pp. 3861-3866.

Balducci et al. "Double-Stranded DNA Diffusion in Slitlike Nanochannels" *Macromolecules* 39:6273-6281 (2006).

Balducci et al. "Conformational preconditioning by electrophoresis of DNA through a finite obstacle array", *Macromolecules*, 2008, vol. 41, pp. 5485-5492.

Brochard et al. "Dynamics of confined polymer chains", J. Chem. Phys., Jul. 1977, vol. 67, pp. 52-56.

Brochard-Wyart et al. "Dynamics of Taut DNA chains", *Europhys. Lett.*, 1999, vol. 47(2), pp. 171-174.

Campbell et al. "Electrophoretic manipulation of single DNA molecules in nanofabricated capillaries", Lab Chip, 2004, 4:225-229.

(56) References Cited

OTHER PUBLICATIONS

Cao et al. "Fabrication of 10 nm enclosed nanofluidic channels", *Applied Physics Letters*, vol. 81, No. 1, Jul. 2002, pp. 174-176.
Cao et al. "Gradient nanostructures for interfacing microfluidics and nanofluidics", *Appl. Phys. Lett.*, Oct. 14, 2002; vol. 81, No. 16, pp. 3058-3060.
Chantiwas et al., "Flexible fabrication and applications of polymer nanochannels and nanoslits", *Chem. Soc. Rev.*, 2011, vol. 40, pp. 3677-3702.
Chou et al. "A microfabricated device for sizing and sorting DNA molecules", *Proc. Natl. Acad. Sci.*, 1999, vol. 96, pp. 11-13.
Cipriany et al. "Single molecule epigenetic analysis in a nanofluidic channel", Anal. Chem., Mar. 15, 2010, vol. 82, No. 6, pp. 2480-2487.
Craddock et al., "Genome-wide association study of CNVs in 16,000 cases of eight common diseases and 3,000 shared controls", *Nature*, 2010, vol. 464, pp. 713-720.
Craighead et al. "Future lab-on-a-chip technologies for interrogating individual molecules" Nature 2006, 442, 387.
Cross et al. "Size-dependent DNA mobility in nanochannels", *Journal of Applied* Physics, 2007, vol. 102, pp. 024701-1-024701-5.
Cui, S.T., "Counterion-Hopping along the Backbone of Single-Stranded DNA in Nanometer Pores: A Mechanism for Current Conduction", *Physical Review Letters*, 2007, vol. 98, pp. 138101-1-138101-4.
Das et al., "Single molecule linear analysis of DNA in nano-channel labeled with sequence specific fluorescent probes", *Nucl. Acids Res.*, 2010, vol. 38, e177, 8 pages.
Dimalanta et al., "A microfluidic system for large DNA molecule arrays", *Anal. Chem.*, 2004, vol. 76, pp. 5293-5301.
Douville et al., "DNA linearization through confinement in nanofluidic channels", *Anal Bioanal Chem.*, 2008, vol. 391, pp. 2395-2409.
Duke et al. "Microchips for Sorting DNA" pp. 11-26 (1997).
Eijkel et al. "Nanofluidics: what is it and what can we expect from it?" Microfluid. Nanofluid. 2005, 1, 249.
Extended European Search Report corresponding to European Patent Application No. 14778772.5 (15 pages) (dated Feb. 7, 2017).
Fan et al. "DNA Translocation in Inorganic Nanotubes", *Nano Letters* 5(9):1633-1637 (2005).
Fischbein et al. "Sub-10 nm Device Fabrication in a Transmission Electron Microscope" Nano Letters 2007, vol. 7, 1329.
Foquet et al., "DNA fragment sizing by single molecule detection in submicrometer-sized closed fluidic channels", *Anal. Chem.*, 2002, vol. 74, pp. 1415-1422.
Freitag et al., "Meandering nanochannels for imaging of ultra-long DNA molecules", *Proceedings of the 15th International Conference on Miniaturized Systems for Chemistry and Life Sciences*, Oct. 2-6, 2011, Seattle, Washington; Landers, J. P., Herr, A., Juncker, D., Pamme, N., Bienvenue, J., Eds.; The Printing House: Stoughton, WI, 2011, pp. 1758-1760.
Gierak et al. "Sub-5 nm FIB direct patterning of nanodevices", *Microelectronic Engineering*, 2007, vol. 84, pp. 779-783.
Gierhart et al. "Nanopore with transverse nanoelectrodes for electrical characterization and sequencing of DNA" Sens. and Actuators B 2008, 132, 593.
Han et al., "Prediction of nanopattern topography using two-dimensional focused ion beam milling with beam irradiation intervals", *Microelectronic Engineering*, 2010, vol. 87, pp. 1-9.
Han et al., "Separation of long DNA molecules in a microfabricated entropic trap Array", *Science*, May 12, 2000; vol. 288, No. 5468, pp. 1026-1029.
Haneveld et al., "Wet anisotropic etching for fluidic 1D nanochannels", *J. Micromech. Microeng.*, 2003, vol. 13, pp. S62-S66.
Holzer et al., "Three-dimensional analysis of porous $BaTiO_3$ ceramics using FIB nanotomography", *Journal of Microscopy*, vol. 216, Pt. 1, Oct. 2004, pp. 84-95.
Huh et al., "Tuneable elastomeric nanochannels for nanofluidic manipulation", *Nature Materials*, vol. 6, Jun. 2007, pp. 424-428.

International Preliminary Report on Patentability Corresponding to International Application No. PCT/US2014/023371; dated Sep. 24, 2015; 12 Pages.
International Search Report and the Written Opinion of the International Searching Authority corresponding to International Patent Application No. PCT/US2014/023371 (16 pages) (dated Jul. 3, 2014).
Jo et al. "A single-molecule barcoding system using nanoslits for DNA analysis", *Proc. Natl. Acad. Sci.*, vol. 104, No. 8, pp. 2673-2678 (2007).
Jo et al. "Elongation and migration of single DNA molecules in microchannels using oscillatory shear flows" *Lab on a Chip* 9:2348-2355 (2009).
Kasianowicz et al. "Nanoscopic Porous Sensors" *Annual Review of Analytical Chemistry* 1:737-766 (2008).
Kim et al., "A highly annotated whole-genome sequence of a Korean individual", *Nature*, 2009, vol. 460, pp. 1011-1015.
Kim et al., "Design and numerical simulation of a DNA electrophoretic stretching device", *Lab Chip*, 2007, vol. 7, pp. 213-215.
Kovarik et al., "Nanofluidics in Lab-on-a-Chip Devices", *Anal. Chem.*, 2009, vol. 81, No. 17, pp. 7133-7140.
Kumar et al., "Origin of translocation barriers for polyelectrolyte chains", J. Chem. Phys. 2009, vol. 131, pp. 194903-1-194903-18.
Lagerqvist et al. "Fast DNA Sequencing via Transverse Electronic Transport", *Nano Letters*, 2006, vol. 6, No. 4, pp. 779-782.
Lam et al., "Genome mapping on nanochannel arrays for structural variation analysis and sequence assembly", *Nat. Biotech.*, Aug. 2012, vol. 30, No. 8, pp. 771-776.
Larson et al., "Single DNA molecule stretching in sudden mixed shear and elongational microflows", *Lab Chip*, 2006, vol. 6, Issue 9, pp. 1187-1199.
Lerman et al. "Why Does the Electrophoretic Mobility of DNA in Gels Vary with the Length of the Molecule?", *Biopolymers*, 1982, vol. 21, pp. 995-997.
Lerman et al., Communications to the Editor "Why Does the Electrophoretic Mobility of DNA in Gels Vary with the Length of the Molecule?" Biopolymers 1982, 21, 995-997.
Levy et al. "Entropic Unfolding of DNA Molecules in Nanofluidic Channels" Nano Letters, 2008, 8, 3839.
Levy et al., "DNA manipulation, sorting, and mapping in nanofluidic systems", Chem Soc Rev 2010; vol. 39, Issue 3, pp. 1133-1152.
Li et al. "Sacrificial polymers for nanofluidic channels in biological applications" Nanotechnology 2003, 14, 578.
Li et al., "Focused ion beam fabrication of silicon print masters", *Nanotechnology*, 2003, vol. 14, pp. 220-223.
Liang et al. "Single Sub-20 nm Wide, Centimeter-Long Nanofluidic Channel Fabricated by Novel Nanoimprint Mold Fabrication and Direct Imprinting", Nano Letters, 2007, vol. 7, 3774.
Liang et al., "Nanogap detector inside nanofluidic channel for fast real-time label-free DNA analysis", Nano Letters, 2008, vol. 8, No. 5, pp. 1472-1476.
Lim et al., "DNA methylation profiling in nanochannels", *Biomicrofluidics*, 2011, vol. 5, 034106, 9 pages.
Lugstein et al., "FIB processing of silicon in the nanoscale regime", *Applied Physics A*, 2003, vol. 76, pp. 545-548.
Maleki et al., "A nanofluidic channel with embedded transverse nanoelectrodes", *Nanotechnology*, 2009, vol. 20:105302, pp. 1-6.
Mannion et al., "Conformational analysis of single DNA molecules undergoing entropically induced motion in nanochannels", *Biophys. J.*, 2006, vol. 90, pp. 4538-4545.
Mao et al. "Fabrication and characterization of 20 nm planar nanofluidic channels by glass-glass and glass-silicon bonding" Lab Chip 2005, 5, 837.
Marie et al. "Nanofluidic devices towards single DNA molecule sequence mapping" *Journal of Biophotonics* 5(8-9):673-686 (2012).
Mark et al., "Microfluidic lab-on-a-chip platforms: requirements, characteristics and applications", *Chem. Soc. Rev.*, 2010, vol. 39, pp. 1153-1182.
McCarroll et al., "Copy-number variation and association studies of human disease", *Nat. Genet.*, 2007, vol. 39, pp. S37-S42.
McCarthy et al., "Microduplications of 16p11.2 are associated with schizophrenia", *Nat. Genet.*, 2009, vol. 41, No. 11, pp. 1223-1227.

(56) References Cited

OTHER PUBLICATIONS

Menard et al., "A Device for Performing Lateral Conductance Measurements on Individual Double-Stranded DNA Molecules", *ACS Nano*, 2012, vol. 6(10), pp. 9087-9094.

Menard et al., "Analysis of Single DNA Molecules Translocating Through Nanochannels Fabricated in $SiO_2$", *Twelfth International Conference on Miniaturized Systems for Chemistry and Life Sciences*, Oct. 12-16, 2008, San Diego, California, 4 pages.

Menard et al., "Electrokinetically-Driven Transport of DNA Through Focused Ion Beam Milled Nanofluidic Channels", *Anal. Chem.*, 2013, vol. 85, pp. 1146-1153.

Menard et al., "Fabrication of Sub-5 nm Nanochannels in Insulating Substrates Using Focused Ion Beam Milling", *Nano Letters*, 2011, vol. 11, No. 2, pp. 512-517.

Menard, Jr. et al., "DNA Transport Characteristics in Focused Beam-Milled Nanofluidic Devices", *2009 Annual Meeting of the American Electrophoresis Society (AES)*, Nov. 10, 2009, Retrieved from the internet at URL http://aiche.confex.com/aiche/2009/webprogram/Paaper160572.html.

Mijatovic et al., "Technologies for nanofluidic systems: top-down vs. bottom-up—a review", *Lab Chip*, 2005, vol. 5, pp. 492-500.

Mills et al., "Mapping copy number variation by population-scale genome sequencing", *Nature*, 2011, vol. 470, pp. 59-65.

Nakayama et al., "Stability and Schottky barrier of silicides: First-principles study", *Microelectronic Engineering*, 2009, vol. 86, pp. 1718-1721.

Nikoobakht, B., "A Scalable Platform for Integrating Horizontal Nanochannels with Known Registries to Microchannels", *Chem. Mater.*, 2009, vol. 21, pp. 27-32.

Orloff et al., "Fundamental limits to imaging resolution for focused ion beams", *Journal of Vacuum Science & Technology B*, Nov./Dec. 1996, vol. 14, No. 6, pp. 3759-3763.

Pang et al. "Fixed-Gap Tunnel Junction for Reading DNA Nucleotides" *ACS Nano* 8(12):11994-12003 (2014).

Perry et al., "Review of fabrication of nanochannels for single phase liquid flow" *Microfluid Nanofluid*, vol. 2:185-193 (2006).

Perry et al. "Ion transport in nanofluidic funnels", *ACS Nano* 4(7):3897-3902 (2010).

Persson et al. "Confinement spectroscopy: probing single DNA molecules with tapered nanochannels" *Nano Letters* 9(4):1382-1385 (2009).

Pinard et al., "Assessment of whole genome amplification-induced bias through high-throughput, massively parallel whole genome sequencing", *BMC Genomics*, 2006, vol. 7, 216, 21 pages.

Pinkel et al., "Comparative genomic hybridization", *Annu. Rev. Genomics Hum. Genet.*, 2005, vol. 6, pp. 331-354.

Pinto et al., "Functional impact of global rare copy number variation in autism spectrum disorders", *Nature*, 2010, vol. 466, pp. 368-372.

Randall et al., "Methods to electrophoretically stretch DNA: microcontractions, gels, and hybrid gel-microcontraction devices", *Lab Chip*, 2006, vol. 6, pp. 516-525.

Randolph et al., "Focused, Nanoscale Electron-Beam-Induced Deposition and Etching", *Critical Reviews in Solid State and Materials Sciences*, 2006, 31:3, pp. 55-89.

Reccius et al., "Conformation, length, and speed measurements of electrodynamically stretched DNA in nanochannels", *Biophys. J.*, Jul. 2008, vol. 95, pp. 273-286.

Reisner et al. "Statics and Dynamics of Single DNA Molecules Confined in Nanochannels", *Physical Review Letters*, vol. 94, pp. 196101-1-196101-4 (2005).

Reisner et al. "Nanoconfinement-Enhanced Conformational Response of Single DNA Molecules to Changes in Ionic Environment", *Physical Review Letters*, vol. 99, pp. 058302-1-058302-4 (2007).

Reisner et al. "Single-molecule denaturation mapping of DNA in nanofluidic channels" *Proceedings of the National Academy of Sciences* 107(30):13294-13299 (2010).

Reisner et al. "DNA confinement in nanochannels: physics and biological applications", *Rep. Prog. Phys.*, vol. 75, Issue 10, 106601, 35 pages (2012).

Riehn et al. "Restriction mapping in nanofluidic devices" *Proceedings of the National Academy of Sciences* 102(29):10012-10016 (2005).

Salieb-Beugelaar et al., "Electrophoretic separation of DNA in gels and nanostructures", *Lab Chip*, 2009, vol. 9, pp. 2508-2523.

Salieb-Beugelaar et al., "Field-Dependent DNA Mobility in 20 nm High Nanoslits", *Nano Letters*, Jul. 2008, vol. 8, No. 7, pp. 1785-1790.

Schoch, R.B., "Transport phenomena in nanofluidics", *Reviews of Modern Physics*, vol. 80, No. 3, Jul.-Sep. 2008, pp. 839-883.

Sebat et al., "Strong association of de novo copy number mutations with autism", *Science*, 2007, vol. 316, pp. 445-449.

Smeets et al. "Salt Dependence of Ion Transport and DNA Translocation through Solid State Nanopores" *Nano Letters* 2006, vol. 6, No. 1, 89.

Smith et al., "Overstretching B-DNA: The elastic response of individual double-stranded and single-stranded DNA molecules", *Science*, 1996, vol. 271, pp. 795-799.

So et al. "Inherently aligned microfluidic electrodes composed of liquid metal", *Lab Chip*, 2011, 11, 905-911.

Sorek et al., "Genome-wide experimental determination of barriers to horizontal gene transfer", *Science*, 2007, vol. 318, pp. 1449-1452.

Speicher et al., "Effect of genome-wide association studies, direct-to-consumer genetic testing, and high-speed sequencing technologies on predictive genetic counselling for cancer risk", *Lancet Oncol.*, Sep. 2010, vol. 11, pp. 890-898.

Stavis et al., "Nanofluidic structures with complex three-dimensional surfaces", *Nanotechnology*, 2009, vol. 20, Issue 16, 165302, 7 pages.

Stefansson et al., "Large recurrent microdeletions associated with schizophrenia", *Nature*, 2008, vol. 455, pp. 232-236.

Striemer et al., "Charge- and size-based separation of macromolecules using ultrathin silicon membranes", *Nature*, Feb. 15, 2007; vol. 445, pp. 749-753.

Strychalski et al., "Diffusion of DNA in Nanoslits", *Macromolecules*, 2008, vol. 41, pp. 7716-7721.

Strychalski et al. "Non-planar nanofluidic devices for single molecule analysis fabricated using nanoglassblowing" *Nanotechnology* 19(16):315301 (2008).

Taniguchi et al., Fabrication of the gating nanopore device, *Applied Physics Letters*, vol. 95, pp. 123701-1-123701-3 (2009).

Teague et al., "High-resolution human genome structure by single-molecule analysis", *Proc. Natl. Acad. Sci.*, vol. 107, pp. 10848-10853 (2010).

Tegenfeldt et al., "The dynamics of genomic-length DNA molecules in 100-nm Channels", *Proc. Natl. Acad. Sci.*, Jul. 27, 2004; vol. 101, No. 30, pp. 10979-10983.

Tong et al., "Silicon Nitride Nanosieve Membrane", *Nano Letters*, 2004, vol. 4, No. 2, pp. 283-287.

Topolancik et al., "Extraction and purification of genomic DNA via entrapment in an array of microposts", *Proceedings of the 15th International Conference on Miniaturized Systems for Chemistry and Life Sciences*, Oct. 2-6, 2011, Seattle, Washington; Landers, J. P., Herr, A., Juncker, D., Pamme, N., Bienvenue, J., Eds.; The Printing House: Stoughton, WI, 2011, p. 1026-1028.

Treangen et al., "Repetitive DNA and next-generation sequencing: computational challenges and solutions", *Nat. Rev. Genet.*, 2011, vol. 13, pp. 36-46.

Tseng, A., "Recent developments in micromilling using focused ion beam technology", *J. Micromech. Microeng.*, 2004, vol. 14, pp. R15-R34.

Tsutsui et al. "Transverse Field Effects on DNA-Sized Particle Dynamics" *Nano Letters* 2009, vol. 9, No. 4, 1659.

Turner et al., "Confinement-induced entropic recoil of single DNA molecules in a nanofluidic structure", *Phys. Rev. Lett.*, 2002, vol. 88, 128103.

USPTO Non-final Office Action for related U.S. Appl. No. 14/204,211, filed Mar. 11, 2014 (11 pages) (dated Jun. 25, 2015).

Utko et al., "Injection molded nanofluidic chips: Fabrication method and functional tests using single-molecule DNA experiments", *Lab Chip*, 2011, vol. 11, pp. 303-308.

(56) References Cited

OTHER PUBLICATIONS

Viero et al. "Hydrodynamic Manipulation of DNA in Nanopost Arrays: Unhooking Dynamics and Size Separation" *Small* 7(24):3508-3518 (2011).

Volkmuth et al. "DNA electrophoresis in microlithographic arrays", *Nature*, Aug. 13, 1992; vol. 358, pp. 600-602.

Wang et al. "Single-molecule studies of repressor-DNA interactions show long-range interactions" *PNAS* 102(28):9796-9801 (2005).

Wang et al. "Manipulating DNA molecules in nanofluidic channels", *Microfluid Nanofluid*, 2:85-88 (2006).

Wanunu, Meni "Nanopores: A journey towards DNA sequencing" *Physics of Life Reviews* 9:125-158 (2012).

Xu et al. "Wide-spectrum, ultrasensitive fluidic sensors with amplification from both fluidic circuits and metal oxide semiconductor field effect transistors" *Applied Physics Letters* vol. 91, pp. 013901-1-013901-3 (2007).

Yuan et al. "Electrokinetic transport and separations in fluidic nanochannels", *Electrophoresis* vol. 28, pp. 595-610 (2007).

Zangle et al., "Theory and experiments of concentration polarization and ion focusing at microchannel and nanochannel interfaces" *Chem. Soc. Rev.* 39:1014-1035 (2010).

Zhou et al. "A whole-genome shotgun optical map of Yersinia pestis strain KIM", *Appl. Environ. Microbiol.*, vol. 68, No. 12, pp. 6321-6331 (2002).

Zhou et al. "Whole-genome shotgun optical mapping of Rhodobacter sphaeroides strain 2.4.1 and its use for whole-genome shotgun sequence assembly", *Genome Res.*, vol. 13, pp. 2142-2151 (2003).

Zhou et al. "A single molecule system for whole genome analysis", *Perspectives in Bioanalysis, vol. 2, New High Throughput Technologies for DNA Sequencing and Genomics*; Mitchelson, K. R., Ed.; Elsevier: Amsterdam; pp. 265-300 (2007).

Zhou et al. "Transport and Sensing in Nanofluidic Devices" *Annual Review of Analytical Chemistry* 4:321-341 (2011).

Zhu et al. "Arrays of horizontally-oriented mini-reservoirs generate steady microfluidic flows for continuous perfusion cell culture and gradient generation" *The Analyst* 129:1026-1031 (2004).

Zwolak, M., "Electronic Signature of DNA Nucleotides via Transverse Transport", *Nano Letters*, 2005, vol. 5, No. 3, pp. 421-424.

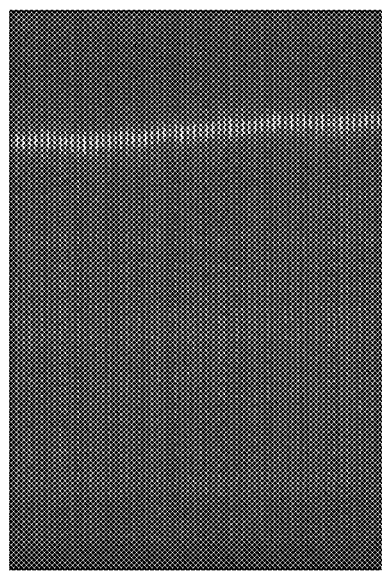
FIG. 10A
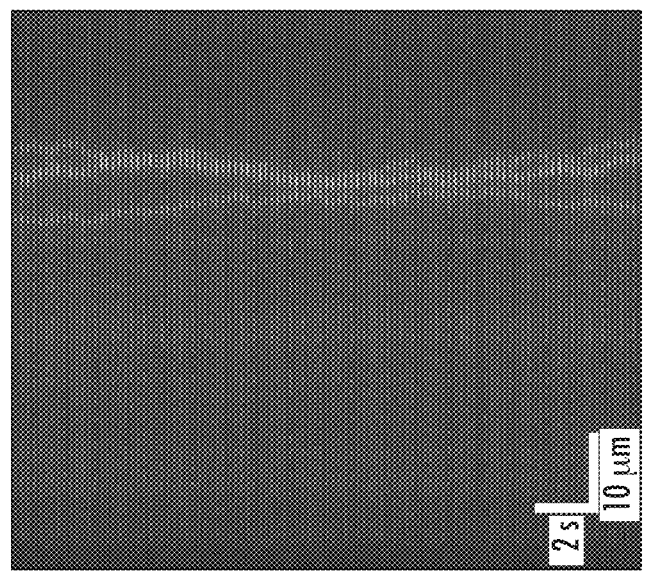
FIG. 10B
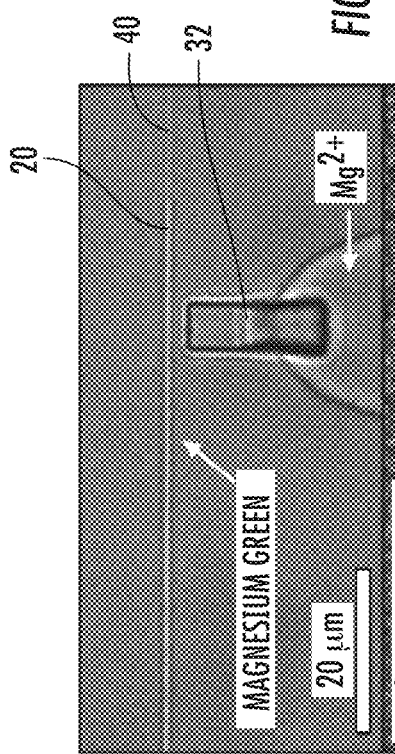
FIG. 9A
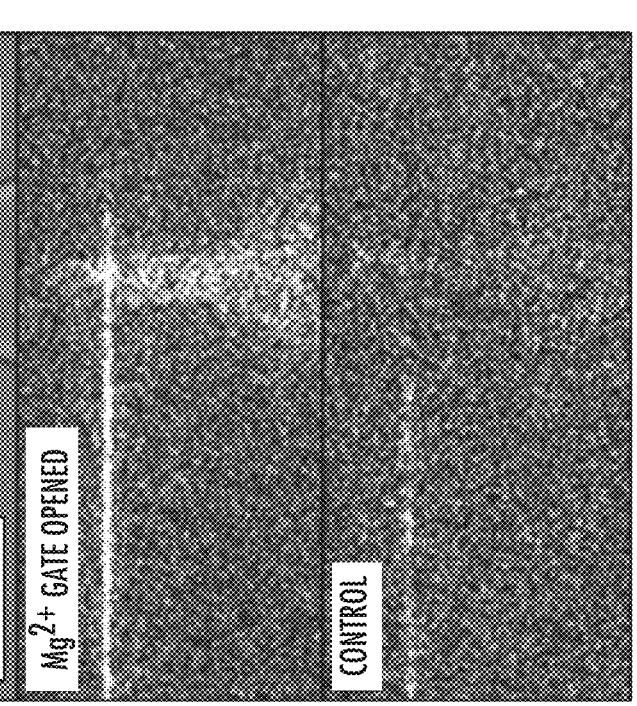
FIG. 9B
FIG. 9C

NANOFLUIDIC DEVICES FOR THE RAPID MAPPING OF WHOLE GENOMES AND RELATED SYSTEMS AND METHODS OF ANALYSIS

RELATED APPLICATIONS

This application is a divisional of U.S. application Ser. No. 14/771,989, filed Sep. 1, 2015, which is a 35 U.S.C. § 371 national phase application of International Application Serial No. PCT/US2014/023371, filed Mar. 11, 2014, which claims the benefit of and priority to U.S. Provisional Application Ser. No. 61/778,746, filed Mar. 13, 2013, the contents of each of which are hereby incorporated by reference as if recited in full herein.

STATEMENT OF FEDERAL SUPPORT

This invention was made with government support under Grant No. HG002647 awarded by the National Institutes of Health. The government has certain rights in the invention.

FIELD OF THE INVENTION

This invention relates to the genomic characterization of polynucleic acids.

BACKGROUND OF THE INVENTION

There has been considerable recent interest in the incorporation of nanoscale components in lab-on-a-chip fluidic devices. This interest owes its origin to several advantages (and differences that may be advantageously leveraged) in moving from the micron scale to the nanoscale. These differences include, for example, double-layer overlap (DLO) and its effect on electro-osmosis and charge permselectivity, localized enhancement of electric fields, higher surface to volume ratios, confinement effects on large synthetic and bio-polymers, and the emerging importance of entropic effects. See, e.g., Yuan et al., *Electrophoresis* 2007, 28, 595-610; Schoch et al., *Rev. Mod. Phys.* 2008, 80, 839-883; and Kovarik et al., *Anal. Chem.* 2009, 81, 7133-7140. Historic examples of nanoscale devices include the use of porous media and gels in chromatographic separations and filtration membranes with nanoscale pores. See, e.g., Lerman et al., *Biopolymers* 1982, 21, 995-997; and Tong et al., *M. Nano Lett.* 2004, 4, 283-287. Recent efforts, however, have been focused on engineering geometrically well-defined conduits for fluid and analyte transport and seamlessly integrating them into devices. See, e.g., Volkmuth et al., *Nature* 1992, 358, 600-602; and Striemer et al., *Nature* 2007, 445, 749-753. The advantage of such regular structures is the relative simplicity of pressure and field gradients, fluid flow, and molecular motion contained within, in contrast to these properties in more tortuous networks. The capability to define, characterize, and easily model these systems can allow a better understanding of separation mechanisms and single molecule physics, for example. See, e.g., Volkmuth et al., *Nature* 1992, 358, 600-602; Reisner et al., *Phys. Rev. Lett.* 2005, 94, 196101; and Salieb-Beugelaar et al., *Lab Chip* 2009, 9, 2508-2523.

Recently FIB milling techniques have been described to form nanofluidic devices. See, Menard et al., Fabrication of Sub-5 nm Nanochannels in Insulating Substrates Using Focused Ion Beam Milling, *Nano Lett.* 2011, 11, 512-517 (published Dec. 20, 2010); and U.S. Provisional Patent Application Ser. No. 61/384,738, filed Sep. 21, 2010 (and related PCT Application PCT/US2011/052127), entitled, Methods, Systems And Devices For Forming Nanochannels, the contents of which are hereby incorporated by reference as if recited in full herein. In addition to FIB milling, a variety of other methods suitable for nanochannel fabrication can be used, including, for example, electron beam lithography, nanoimprint lithography, photolithography, templating or molding strategies, and other methods understood by one of ordinary skill in the art.

A number of nanofluidic devices have been proposed, including those with integrated miniature electrodes (nano- or micro-scale) for single-molecule sensing and/or nucleic acid sequencing. Alternatively, integrated devices consisting of entirely fluidic components can provide greater control of single-molecule transport and detection. See, Menard et al., A Device for Performing Lateral Conductance Measurements on Individual Double-Stranded DNA Molecules, ACS Nano 2012, 12, 9087-9094 (published Sep. 5, 2012); U.S. Provisional Patent Ser. No. 61/533,523, filed Sep. 12, 2011 (and corresponding pending PCT/US13/054128), entitled, Devices with a Fluid Transport Nanochannel Intersected by a Fluid Sensing Nanochannel and Related Methods; and U.S. Provisional Patent Ser. No. 61/770,586, filed Feb. 28, 2013, entitled Nanofluidic Devices with Integrated Components for the Controlled Capture, Trapping, and Transport of Macromolecules and Related Methods of Analysis, the contents of which are hereby incorporated by reference as if recited in full herein. Such integration of components on a single monolithic device can enable new methods and systems that address current analysis needs in fields such as DNA sequencing and medical diagnostics.

SUMMARY OF EMBODIMENTS OF THE INVENTION

Embodiments of the invention are configured to provide devices that facilitate high throughput restriction mapping of chromosomal DNA.

Embodiments of the invention include nanofluidic analysis systems. The systems include: (a) a reaction nanochannel that is between 500 µm and 10 cm long and that merges into a detection nanochannel at an interface position therebetween where the detection nanochannel reduces in size relative to the reaction nanochannel; (b) a microfluidic channel in communication with an ingress portion of the reaction nanochannel; (c) a first electrode in communication with the microfluidic channel; (d) a first transverse fluidic channel extending from and in fluid communication with the reaction nanochannel at a location that is spaced apart from but proximate the ingress portion of the reaction nanochannel; (e) a second electrode in communication with the first transverse fluidic channel; (f) a second transverse fluidic channel extending from and in fluid communication with the reaction nanochannel downstream of the first transverse fluidic channel; (g) a third electrode in communication with the second transverse fluidic channel; (h) a fourth electrode in communication with the detection nanochannel; (i) a circuit configured to control operation of the first, second, third and fourth electrodes to controllably thread, load and digest DNA within the reaction nanochannel that prevents fragment disordering (e.g., DNA is reacted in the reaction nanochannel producing ordered fragments); and (j) an electrical or optical detector in communication with the detection nanochannel configured to spatially and temporally resolve fragment size to thereby allow an ordered restriction map of chromosomal DNA in real time or near real time.

The microfluidic channel can include an array of spaced apart posts configured to partially occlude the microfluidic flow path.

The system can include a nanofunnel connecting the microfluidic channel with the ingress portion of the fluid transport nanochannel.

The nanofluidic reaction channel can have a serpentine shape with a plurality of closely spaced substantially parallel segments connected by "U" shaped segments.

The microfluidic channel, the reaction nanochannel, the detection nanochannel and the first and second fluidic transverse channels can be monolithically integrated on a fluidic chip.

The first and/or second transverse fluidic channel can be a fluidic nanochannel with depths between about 1 nm and about 100 nm and widths between about 20 nm and about 2000 nm.

The reaction nanochannel can be between 10 and 1000 times longer and between 2 and 10 times larger in depth and/or width than the detection nanochannel.

The microfluidic channel can be in fluid communication with one or more reservoirs, at least one of which includes whole cells for DNA analysis.

The whole cells for analysis can be restrained by a gel matrix for the extraction of genomic DNA.

The whole cells for analysis can be restrained by at least one high and/or low-density post array in the microfluidic channel to facilitate extraction of genomic DNA.

The microfluidic ingress channel includes whole cells with DNA. The second transverse fluidic channel merges into a second fluid reservoir at an end portion away from the reaction nanochannel. The second fluid reservoir holds a solution of restriction endonuclease and cofactor.

The reaction nanochannel can be straight and can have a length between about 500 μm to about 2 cm. The reaction nanochannel can be between about 10 and about 1000 times longer and between about 2 and about 10 times larger in depth and/or width than the detection nanochannel.

The system may include a second reaction nanochannel that is in fluid communication with the fluid microchannel on an ingress end of the second reaction nanochannel and that merges into a respective second detection nanochannel at an opposing egress end of the second reaction nanochannel.

Other embodiments are directed to nanofluidic analysis chips. The chips include: (a) a microfluidic inlet adapted to extract genomic DNA from whole cells, nuclei, whole chromosomes, or other sources of long DNA molecules with a microfluidic channel having an array of posts; (b) a reaction nanochannel that is between 500 μm and 10 cm long, the reaction nanochannel having an ingress portion that connects to the microfluidic inlet; (c) a detection nanochannel that merges with an egress end of the reaction nanochannel at an intersection defined by a reduction in nanochannel size; (d) a first transverse nanochannel extending from and in fluid communication with the reaction nanochannel that is spaced apart from but proximate an ingress portion of the reaction nanochannel; and (e) a second transverse fluidic nanochannel extending from and in fluid communication with the reaction nanochannel downstream of the first transverse fluidic nanochannel.

The chip can also include a nanofunnel residing between and connecting the reaction nanochannel with the microfluidic inlet.

The chip can include a plurality of reservoirs, including at least one in fluid communication with the microfluidic inlet, at least one in fluid communication with the first transverse nanochannel, at least one in fluid communication with the second transverse nanochannel, and at least one in fluid communication with an end of the detection nanochannel.

The array of posts in the microfluidic channel can include multiple segments of arrays that are axially spaced apart.

The array of posts can be configured to extend across substantially an entire width of the microfluidic channel.

Still other embodiments are directed to methods of generating an ordered restriction map of genomic DNA extracted from whole cells, nuclei, whole chromosomes, or other sources of long DNA molecules. The methods include: (a) providing a device having a fluidic microchannel that merges into a reaction nanochannel that merges into a detection nanochannel at an interface where the nanochannel diameter decreases in size; (b) lysing whole cells and dechromatinizing DNA with minimal fragmentation in the microchannel; then (c) introducing an intact molecule of DNA to the reaction nanochannel; then (d) fragmenting the intact DNA in the reaction nanochannel using restriction endonuclease enzymes. The reaction nanochannel is sized and configured so that the fragments stay in an original order until they are injected into the detection nanochannel. The method further includes (e) detecting signal at one or more locations along the detection nanochannel to map fragments in the order they occur along a long DNA molecule.

The device can include at least one reservoir in fluid communication with a fluidic microchannel that merges into the reaction nanochannel. The introducing step can be carried out by introducing whole cells, nuclei, whole chromosomes, or other sources of long DNA molecules for analysis using the reservoir. The method can also include providing a gel matrix and/or high-density post array for immobilizing the whole cells, then lysing the cells, extracting the DNA, and, optionally, staining the DNA, then introducing the intact molecule of DNA into the reaction nanochannel.

The device can include a microfluidic channel with an array of posts that is in fluid communication with an ingress end of the reaction nanochannel and a first transverse channel in fluid communication with the reaction channel downstream of the microfluidic channel.

The method can include threading and loading the sample by applying a voltage to the microfluidic and transverse channels to create a bias at the ingress region of the reaction nanochannel.

The threading step can be carried out using controlled voltage or concentration polarization gradients proximate the ingress of the reaction channel so that initially the DNA molecule is not subjected to a strain that exceeds DNA tensile strength and does not mechanically break.

After the threading step, the loading can be carried out by changing the voltages applied to the reaction nanochannel and transverse nanochannels to pull the full DNA molecule into the reaction nanochannel at a velocity that is between about 1 μm/s and about 1 mm/s, such that a trailing end of the DNA molecule has sufficient time to disengage diffusively from any post entanglements and mechanical breakage is avoided.

The reaction of restriction digestion can be carried out by changing the voltages applied to the reaction nanochannel and transverse nanochannels to introduce restriction endonuclease and cofactor to the DNA contained in the reaction nanochannel, then a reaction is allowed to progress until all restriction sites have been digested.

The voltages applied to the reaction nanochannel and transverse nanochannels can inhibit or prevent the introduction of restriction endonuclease and cofactor to the microfluidic channel and thus prevent the digestion of DNA molecules external to the reaction nanochannel.

The detection of the ordered restriction fragments can be carried out by changing the voltages applied to the reaction nanochannel and transverse nanochannels to drive migration of the fragments to the interface between the reaction nanochannel and the detection nanochannel.

In some embodiments, the threading, loading, restriction digestion, and ordered detection of restriction fragment sizes can be realized using continuously applied constant voltages.

The detection nanochannel diameter can decreases in size by between 50% to 99% from the reaction nanochannel thereby resulting in an increase in transport velocity as each fragment reaches the intersection and the separation of each neighboring fragment. Then the detecting step can be carried out to detect transport of the separated fragments through the detection nanochannel.

The detecting step can be carried out by detecting the fragments optically or electrically at one or more locations along the detection nanochannel.

The method can include determining fragment size by analyzing a detected signal duration or integrated amplitude.

The device can be a fluidic analysis chip.

The chip can be used in combination with a transport system that is in communication with the chip, wherein the transport system is configured to apply at least one of electrokinetic, pressure, or centripetal forces to cause transport genomic DNA and fragments thereof through the reaction nanochannel into the detection nanochannel.

Yet other embodiments are directed to methods for interfacing with fluidic analysis chips. The methods include: (a) controlling sample introduction, cell lysis, and DNA extraction and staining; (b) DNA threading and loading extracted DNA into the reaction nanochannel, restriction digestion with restriction endonuclease and cofactor in the reaction nanochannel, and an ordered transport of restriction fragments through the detection nanochannel; (c) electronically detecting restriction fragments during transport through the detection nanochannel; (d) electronically analyzing restriction fragment sizes from DNA molecules using real time or near real time analysis; and (e) electronically generating consensus restriction maps from multiple DNA molecules and assessing map quality to evaluate the need for additional sampling.

Still other aspects of the invention are directed to systems for interfacing with fluidic analysis chips. The systems include: (a) means for controlling sample introduction, cell lysis, and DNA extraction and staining; (b) means for controlling DNA threading and loading into the reaction nanochannel, restriction digestion with restriction endonuclease and cofactor in the reaction nanochannel, and an ordered transport of restriction fragments through the detection nanochannel; (c) means for detecting restriction fragments during transport through the detection nanochannel; (d) means for analyzing restriction fragment sizes from DNA molecules using real time or near real time analysis; and (e) means for generating consensus restriction maps from multiple DNA molecules and assessing map quality to evaluate the need for additional sampling.

Still other embodiments are directed to fluidic analysis devices. The devices include a microfluidic channel having a flow path merging into a reaction nanochannel; a DNA reservoir in fluid communication with the microfluidic channel upstream of the reaction nanochannel; a threading reservoir in fluid communication with the reaction nanochannel residing proximate the inlet of the reaction nanochannel; a detection nanochannel connected to an egress end of the reaction nanochannel having a smaller diameter and/or smaller width and depth than the reaction nanochannel; and a reservoir comprising restriction endonuclease and cofactor in fluid communication with the reaction nanochannel, residing proximate the detection nanochannel.

The device may optionally include a second reaction nanochannel that is between about 500 µm and 10 cm long that is in fluid communication with and that resides downstream of the first reaction nanochannel after the second transverse fluid nanochannel. The chip may be in communication with a circuit that selectively directs restriction fragments from the first reaction nanochannel to either fluidically enter a waste outlet path or fluidically enter the second reaction nanochannel.

The chip may include a waste outlet path and a plurality of collection reservoirs with associated outlet channels that extend downstream of the second transverse fluid nanochannel. The chip can be in communication with a circuit that selectively directs restriction fragments from the first reaction nanochannel to either enter the waste outlet path or one of the collection reservoirs.

The chip can include a second reaction nanochannel that is between 500 µm and 10 cm long that is in fluid communication with and that resides downstream of the first reaction nanochannel after the second transverse fluid nanochannel. The chip can be in communication with a circuit that selectively directs restriction fragments from the first reaction nanochannel to either fluidically enter a waste outlet path or fluidically enter the second reaction nanochannel.

The chip can include a waste outlet path and a plurality of collection reservoirs with associated outlet channels that extend downstream of the second transverse fluid nanochannel. The chip can be in communication with a circuit that selectively directs restriction fragments from the first reaction nanochannel to either enter the waste outlet path or one of the collection reservoirs.

The methods can include electronically or optically identifying when regions of interest are being mapped in real time or near real time and selectively and automatically transporting restriction fragments fluidically to a second nanoreaction channel when regions of interest are detected as being mapped.

The methods can include electronically or optically identifying when regions of interest are being mapped in real time or near real time and automatically and selectively transporting restriction fragments of interest fluidically to respective outlet channels into respective collection reservoirs for later analysis and fluidically transporting other restriction fragments to a waste outlet channel.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim and/or file any new claim accordingly, including the right to be able to amend any originally filed claim to depend from and/or incorporate any feature of any other claim or claims although not originally claimed in that manner. These and other objects and/or aspects of the present invention are explained in detail in the specification set forth below. Further features, advantages and details of the present invention will be appreciated by those of ordinary skill in the art from a reading of the figures and the detailed description of the preferred embodiments that follow, such description being merely illustrative of the present invention.

BRIEF DESCRIPTION OF THE DRAWINGS

FIG. 9A is a bright field optical image of the intersection of the reaction nanochannel with the nanochannel for introducing $Mg^{2+}$ according to embodiments of the present invention.

FIG. 9B is a difference image of the region of the device shown in FIG. 9A showing the increase in Magnesium Green fluorescence upon voltage-gated introduction of $Mg^{2+}$ ions according to embodiments of the present invention.

FIG. 9C is a difference image of the region of the device shown in FIG. 9A showing minimal change in Magnesium Green fluorescence when the open gate voltages were applied but no $Mg^{2+}$ was present in the side nanochannel according to embodiments of the present invention.

FIG. 10A is a series of fluorescence images showing the diffusion of λ-DNA in a reaction nanochannel.

FIG. 10B is a series of fluorescence images showing that after about a 1.5 minute digestion by a restriction endonuclease in the presence of $Mg^{2+}$ three fragments are observable. Fragment order was retained despite the fragments' high diffusivity.

DESCRIPTION OF EMBODIMENTS OF THE INVENTION

Figure 1A:
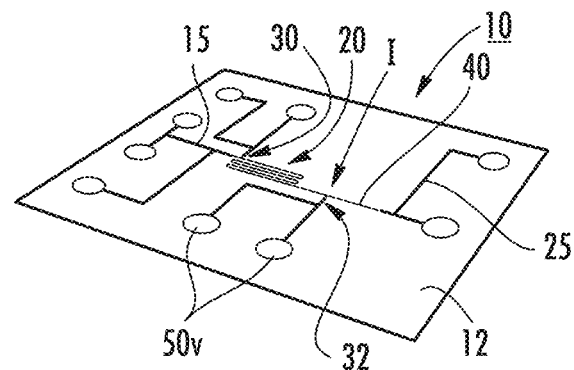
FIG. 1A is a schematic illustration of a fluidic analysis device according to embodiments of the present invention.

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain layers, components or features may be exaggerated for clarity, and broken lines illustrate optional features or operations unless specified otherwise. In addition, the sequence of operations (or steps) is not limited to the order presented in the figures and/or claims unless specifically indicated otherwise. In the drawings, the thickness of lines, layers, features, components and/or regions may be exaggerated for clarity and broken lines illustrate optional features or operations, unless specified otherwise.

The terminology used herein is for the purpose of describing particular embodiments only and is not intended to be limiting of the invention. As used herein, the singular forms, "a", "an" and "the" are intended to include the plural forms as well, unless the context clearly indicates otherwise. It will be further understood that the terms "comprises," "comprising," "includes," and/or "including" when used in this specification, specify the presence of stated features, regions, steps, operations, elements, and/or components, but do not preclude the presence or addition of one or more other features, regions, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

It will be understood that when a feature, such as a layer, region or substrate, is referred to as being "on" another feature or element, it can be directly on the other feature or element or intervening features and/or elements may also be present. In contrast, when an element is referred to as being "directly on" another feature or element, there are no intervening elements present. It will also be understood that, when a feature or element is referred to as being "connected", "attached" or "coupled" to another feature or element, it can be directly connected, attached or coupled to the other element or intervening elements may be present. In contrast, when a feature or element is referred to as being "directly connected", "directly attached" or "directly coupled" to another element, there are no intervening elements present. Although described or shown with respect to one embodiment, the features so described or shown can apply to other embodiments.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. Well-known functions or constructions may not be described in detail for brevity and/or clarity.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

The term "nanochannel" refers to a channel or trench having a critical dimension that is at a nanometer scale. The nanochannel has sidewalls and a floor. The nanochannel can be formed into a solid substrate to have an open top surface and a closed bottom surface with the sidewalls extending therebetween. A cover may be used to seal or otherwise close the upper surface of the nanochannel(s). The term "primary dimension" refers to a width and/or depth dimension. The primary dimensions of a fluid transport nanochannel can be between about 1 nm to about 500 nm. Different nanochannels can have different primary dimensions. The primary (also known as "critical") dimensions of the reaction nanochannel can be between about 300-400 nm and the reaction nanochannel can be between about 10 nm to about 300 nm.

The term "about" refers to parameters that can vary between +/−20% or less, such as +/−10%.

The term "transverse" nanochannel refers to a fluidic nanochannel that crosses a respective fluid transport nanochannel.

The term "fluid transport nanochannel" refers to a nanochannel therethrough which an analyte flows for analysis. In certain embodiments, the fluid transport nanochannel can have two primary segments, a reaction nanochannel and a detection nanochannel. The analyte can be any analyte of interest including, for example, single analyte molecules including synthetic and biological macromolecules, nanoparticles, small molecules, DNA, nucleic acids/polynucleic acids, peptides, proteins and the like. The transport through the nanochannel can be carried out using electrokinetics, concentration polarization and/or hydraulic pressure (forced pressure or pressure gradients).

The term "upstream" indicates a relative position that is closer to the fluid transport nanochannel or reaction channel ingress. The term "downstream" indicates a relative position that is closer to the fluid transport nanochannel or reaction channel egress.

The term "shallow" refers to nanochannel depths that have a lesser depth than a transport nanochannel and that are smaller than analyte macromolecules' hydrodynamic sizes. With respect to the depth of the reaction nanochannel, a shallow nanochannel has a depth that is typically less by at least a factor of 2, such as by between 2-100×. Thus, for example, a shallow nanochannel segment can be 10 nm or less, typically between about 0.1 nm and 9 nm, while the transport nanochannel can have a depth (at least adjacent the shallow segment) that is 20 nm or more, such as between 20-100 nm.

The term "long" with respect to the reaction nanochannel 20 means that the reaction nanochannel is between 10 and 1000 times the length of the detection nanochannel 40. The reaction nanochannel 20 can be longer and between 2 and 10 times larger in depth and/or width than the detection nanochannel 40. The reaction nanochannel 20 can, in some embodiments have a length between about 500 μm and 10 cm long.

The term "wide" means that the nanochannel has a width that is at least 2× (two times, "X" means "a multiplier" or "times") that of a width of the transport nanochannel that it cooperates with to perform the analysis (e.g., provide a driving voltage), and more typically between 3×-100×, such as 3×, 4×, 5×, 6×, 7×, 8×, 9×, about 10×, about 20×, about 40×, about 50×, about 60×, about 70×, about 80×, about 90×, or about 100× the width of the adjacent cooperating reaction nanochannel.

The term "circuit" refers to an entirely hardware embodiment or an embodiment combining software and hardware.

The term "high density" with respect to the posts means that the arrays extend across the entire width of a microchannel and the posts are arranged with an edge-to-edge spacing that is less than about 10 μm. The term "low density" means that the posts are arranged with an edge-to-edge spacing that is typically greater than about 50 μm.

The term "low velocity" means that the macromolecule moves through the nanochannel at a velocity that is between about 1 μm/s and about 1 mm/s.

The term "significantly different field strengths" means that one side of the fluid transport nanochannel can have a voltage/cm field strength that is 10×-1000×, typically 100×-200×, greater or smaller than a second segment of that same channel.

The term "thread" and derivatives thereof means the process by which the analyte molecule is initially introduced to the reaction nanochannel 20, providing for the linearization of a macromolecule from the random coil conformation realized in the microchannel or reservoir. The term "load" means that an analyte molecule present in a microchannel or reservoir accessing the entrance(s) to the reaction nanochannel 20 is successfully introduced to the reaction nanochannel 20 in its entirety and in a linear, post-thread configuration.

The term "react" and derivatives thereof means that DNA is fragmented using restriction endonuclease enzymes and an optional cofactor. Thus, for example, the restriction digestion of DNA within the reaction nanochannel prevents fragment disordering (e.g., DNA is reacted in the reaction nanochannel producing ordered fragments). For example, $Mg^{2+}$ is a cofactor for a Type II class of restriction endonucleases that may be particularly suitable for embodiments of the present invention. The fact that the cofactor is charged can aid in voltage gating of the second transverse channel 32. The majority of restriction endonucleases that are available are Type II. Other types (Types I, III, IV) may also be suitable and have different cofactors (ATP, S-adenosyl-L-methionine) that may be controlled in a similar manner. Thus, while preferred, embodiments of the invention are not limited to Type II with a $Mg^{2+}$ cofactor.

The term "size" means that fragments are pulled into the detection nanochannel, creating separation from neighbors for the determination of the size of fragments by detecting electrical or optical signal duration or amplitude.

The term "chromosomal DNA" means an entire chromosome's complement of DNA or a fragment of same.

Embodiments of the invention are directed to genomic mapping of DNA in a nanofluidic device.

Figure 1B:
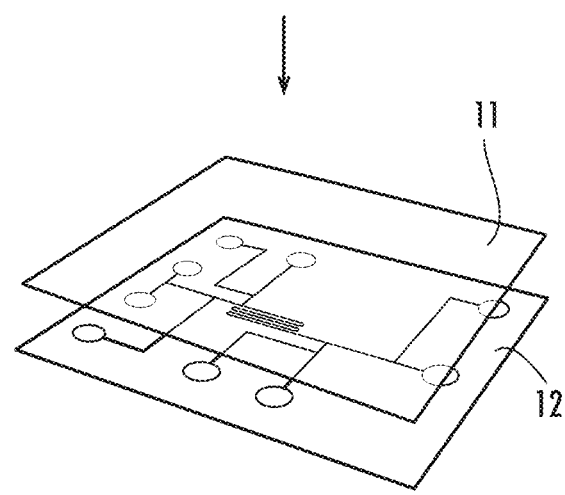
FIG. 1B illustrates a cover plate can be bonded to the device shown in FIG. 1A according to embodiments of the present invention.
Figure 1C:
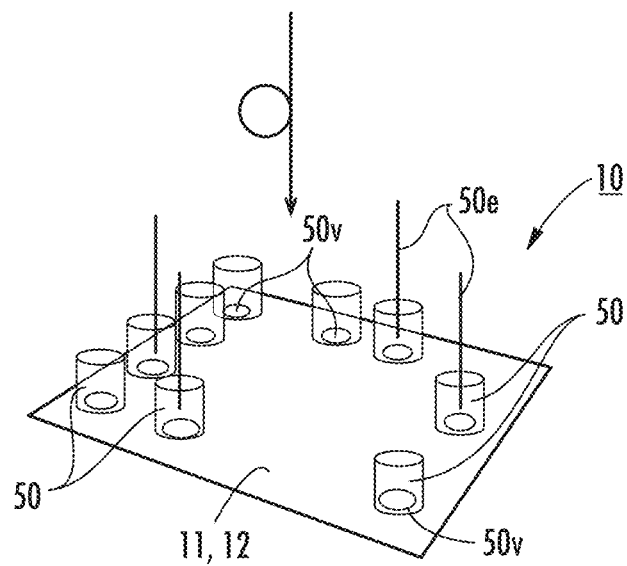
FIG. 1C illustrates that reservoirs may be attached to the device shown in FIG. 1B according to some embodiments of the present invention.

FIGS. 1A-1C illustrate an exemplary nanofluidic analysis device 10. In this embodiment, the device 10 can be a chip with a pattern of microchannels 15 and nanochannels 20, 30, 32 and 40. FIG. 1B illustrates a cover 11 that can be attached (typically bonded) to a substrate 12 with the pattern of channels. FIG. 1C illustrates reservoirs 50 or "R" can be attached to the device 10. As shown, the device 10 includes a microfluidic channel 15 that connects to an ingress end of the (long) reaction nanochannel 20. The detection nanochannel 40 is not required to be inline with the reaction channel 20 and can angle away from or otherwise extend from the reaction nanochannel. The other end of the reaction channel 20 merges into a detection nanochannel 40 at an interface I that is defined by a reduction in size, e.g., width/depth and/or diameter of the nanochannel. A first transverse channel 30 extends off the reaction nanochannel 20 proximate the ingress end of the reaction nanochannel, typically within about 10-500 μm downstream of the nanofunnel 17 (where used) and/or ingress portion of the reaction nanochannel 15e.

A second transverse channel 32 extends off the reaction nanochannel 20 downstream of the first transverse channel 30 and before the interface I.

In some embodiments, the monolithic integration of a number of nanofluidic components results in the rapid generation of genome level maps of DNA extracted from whole cells using the nanofluidic device 10.

Generally stated, a suspension of whole cells can be introduced to a microfluidic input (one or more of the reservoirs 50) on the device 10. The cells are lysed and the DNA is dechromatinized and, in some embodiments, fluorescently stained. In some embodiments, fluorescent stains can be introduced to intact DNA prior to restriction digestion or to the ordered fragments after restriction digestion using microfluidic or nanofluidic elements located downstream of the DNA extraction elements and/or reaction nanochannel Chromosomal DNA is then introduced to a long reaction nanochannel 20, which extends the molecule and prevents the diffusive mixing of fragments generated in the subsequent steps. A solution of restriction endonuclease and cofactor is then introduced to the reaction nanochannel 20, resulting in the digestion of the DNA at sequence specific restriction sites. The lengths of these fragments are then analyzed by transporting the ordered fragments contained in the reaction nanochannel 20 to the intersection I where the reaction nanochannel 20 is interfaced to the detection nanochannel 40. The force driving transport (e.g., electrostatic, pressure, or centripetal) is greater in the detection nanochannel 40 than in the reaction nanochannel 20, resulting in an increase in transport velocity as each fragment reaches the intersection and the separation of each fragment from its neighbors. The spatially and temporally resolved fragments are detected downstream in the detection nanochannel 40 using imaging or single point or multiple point detection (electrical or optical) and the resulting signal analyzed to determine the fragment size. In this fashion, an ordered restriction map of chromosomal DNA can be produced in real time or near real time. The term "near real time" means in a time that is within about 1 minute of real time due to bandwidth of operational systems or other analysis-related computation or lag time.

In some embodiments described herein, device operations are primarily electrostatically controlled using voltages applied at the various fluidic inlets but other forces (e.g., pressure or centripetal) can also be used as will be recognized by those of skill in the art.

Device Fabrication

Fluidic devices can be fabricated in a variety of substrates including silicon, glass (silica), quartz, plastics, thermoplastics, and elastomers or a combination thereof. FIGS. 1A-1C show an example device fabrication workflow. Microfluidic components 25 shown by the larger/wider/darker lines that facilitate DNA extraction and provide an interface to the device's nanofluidic elements can be patterned using established methods such as photolithography and wet or dry etching, molding, embossing, or machining. The nanofluidic elements 20, 30, 32, 40, can be fabricated using a variety of methods including photolithography, electron beam lithography, or nanoimprint lithography followed by etching; focused ion beam milling; electron beam milling; molding; or embossing. Once the fluidic elements are fabricated in the top surface of the substrate 12, a cover plate 11 can be attached, typically bonded to the substrate to form the enclosed fluidic network using, for example, fusion bonding, anodic bonding, or bonding with an adhesive film between the bottom substrate and cover plate. The microchannels can be accessed through vias that pass through the bottom substrate and/or top cover plate. Reservoirs 50 can be affixed to the device over the vias 50v to facilitate liquid handling. Electrodes 50e can be inserted into all or selected reservoirs 50. The reservoirs 50 have vias 50v. The electrodes 50e apply voltages across the various fluidic elements. Air or vacuum lines can be coupled to the reservoirs or vias to apply positive pressure or vacuum to the fluidic elements and drive pressure-driven fluid flow.

DNA Extraction

Figure 2A:
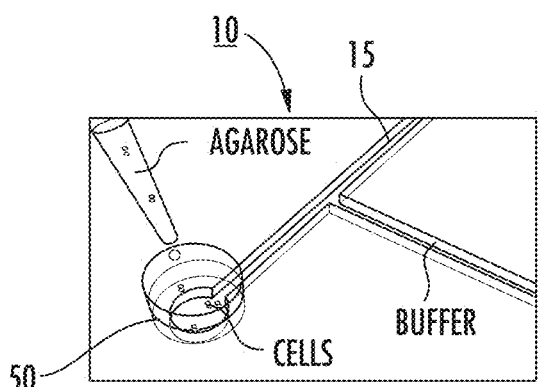
FIGS. 2A-2D illustrate an on-chip process of DNA extraction according to embodiments of the present invention.
Figure 2B:
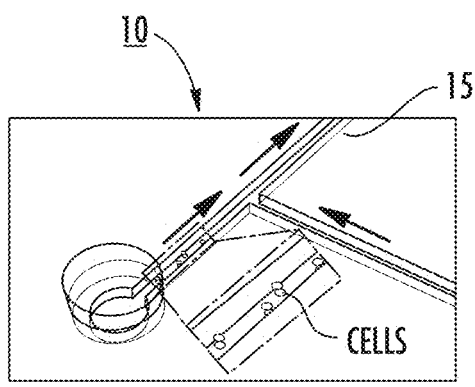
Figure 2C:
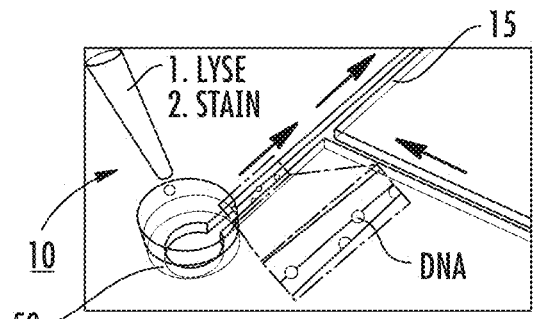
Figure 2D:
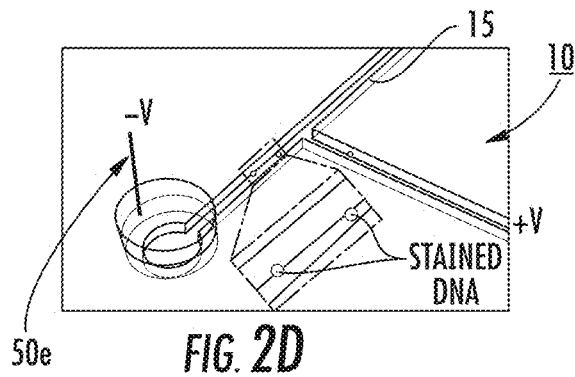

The encapsulation of cells in gelling media before or during their introduction to a fluidic device, or their capture in a network of nanometer or micrometer-scale fabricated structures enables the extraction of chromosomal DNA from the cells with little or no fragmentation. As an example, the use of low melting point agarose gel for the manipulation of cells is shown in FIG. 2A-2D. Cells in low melting point agarose are introduced to a microfluidic reservoir (FIG. 2A) and then pulled into the inlet microfluidic channel while the agarose is still melted, using a syringe pump withdrawing from the channel outlet (FIG. 2B). The agarose is allowed to gel, encapsulating and protecting the DNA during subsequent treatments. Solutions are introduced to digest the cell wall (for microbes and plant cells) then to chemically lyse the cell using detergent solutions incorporating agents such as proteinase K to inhibit native nuclease activity (FIG. 2C). The gel is rinsed thoroughly with buffer, followed by a solution of intercalating dye. Incorporating these tasks on a chip enables the precise control of flow rates and eliminates any turbulence that might otherwise contribute to DNA shearing. The gel is melted by heating the device (it may be further disrupted by adding the enzyme agarase) and the dechromatinized DNA extracted from the matrix electrophoretically (FIG. 2D). The uncharged agarose is excluded from the nanofluidic region of the device by electroosmotic flow. Restriction endonuclease can be added to the DNA before it encounters the nanofluidic channels through a separate inlet microchannel (not shown).

Figure 3A:
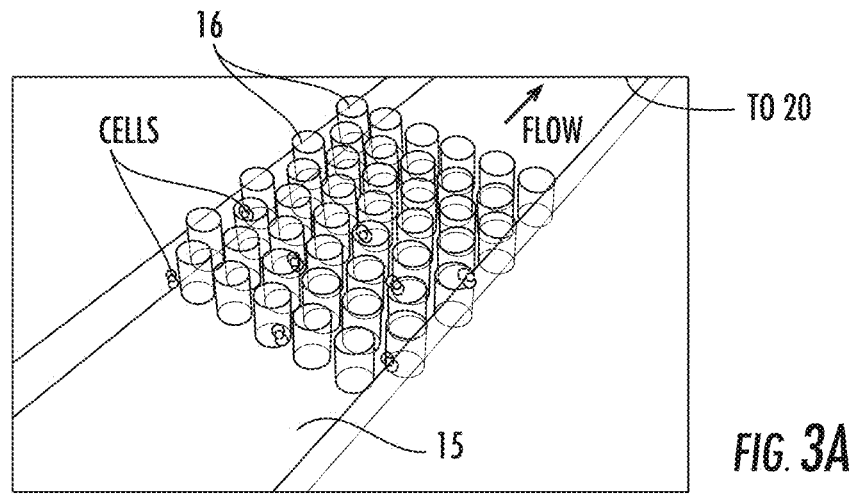
FIGS. 3A-3C are schematic illustrations of an enlarged microfluidic portion of a device showing capturing of whole cells, lysis and staining of dechromatinized DNA according to embodiments of the present invention.
Figure 3B:
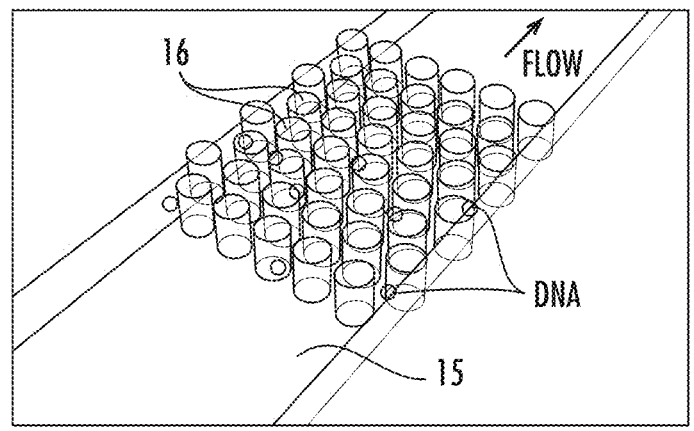
Figure 3C:
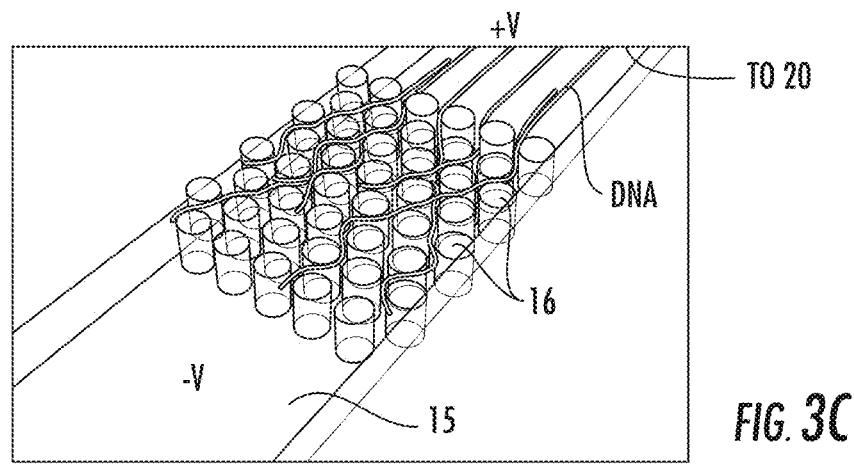

Alternative approaches to the agarose encapsulation indicated here include using a microfabricated high density post array 16 to trap cells introduced to the device using pressure-driven flow, lysing the cells, and then capturing the DNA by entanglement within the post array (FIGS. 3A-3C). FIG. 3A shows capture of whole cells. FIG. 3B shows lysis of cells and staining of dechromatinized DNA using low flow rates and/or diffusive mixing of reagents. FIG. 3C illustrates extraction of the DNA from the post array 16 using an applied voltage. The posts 16 can be circular or have other geometries, typically without sharp edges. The posts 16 can have the same height as the depth of the fluidic microchannel 15. The posts can have small spaces therebetween to allow for an uncoiled length of the DNA to travel therebetween. In some embodiments, the posts 16 can have a width of between about 1-10 µm, typically about 5 µm with spacing between posts greater or lesser than the width of the posts, typically between about 2-50 µm, such as about 10 µm.

Figure 4A:
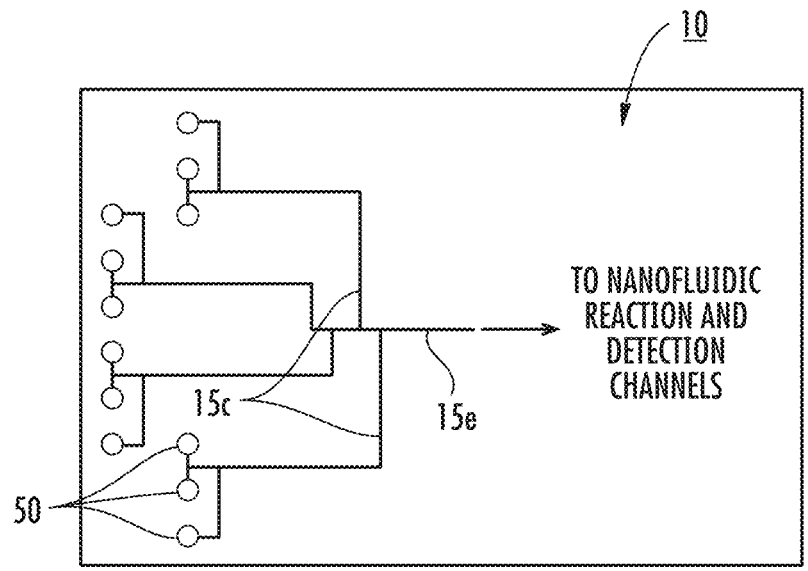
FIG. 4A is a schematic illustration of a fluidic analysis device with an exemplary pattern of sample inlets that lead to the nanofluidic reaction channel according to embodiments of the present invention.

A pattern of multiple fluid inputs 15a of microfluidic channels 15c and reservoirs 50 can also be used for sample introduction and DNA extraction for analyses requiring more material (FIG. 4A).

Figure 4B:
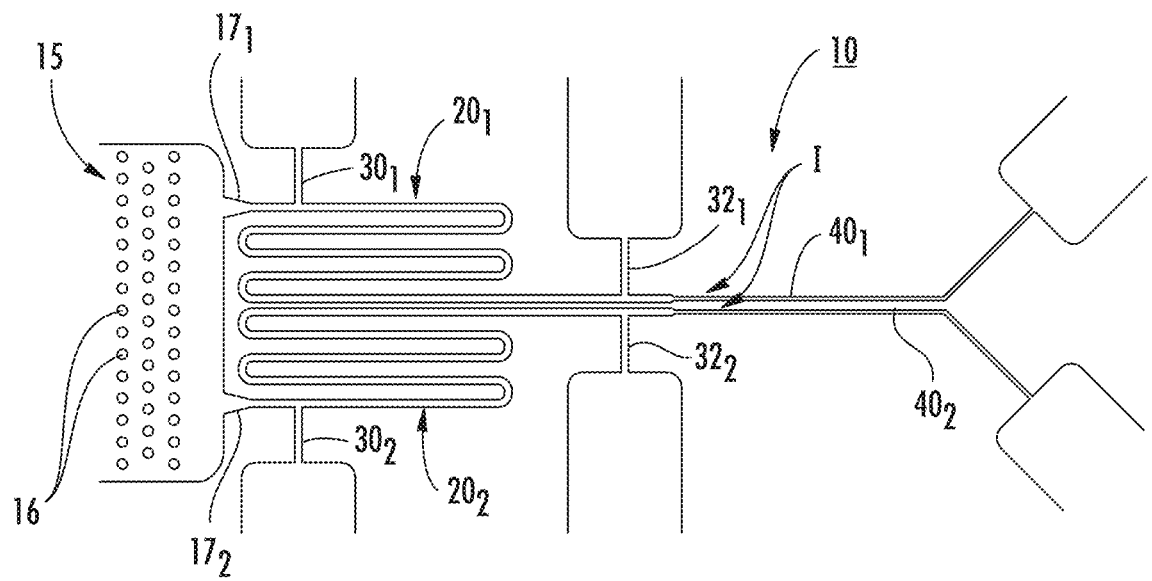
FIG. 4B is a schematic illustration of a fluidic analysis device with multiple reaction nanochannels and respective detection nanochannels in fluid communication with a common microchannel through which sample DNA molecules are introduced according to some embodiments of the present invention.

FIG. 4B illustrates that the device 10 can include a plurality of reaction nanochannels fed DNA from a single microchannel 15 to increase processing speeds. Although shown as two reaction nanochannels $20_1$, $20_2$ merging into respective detection nanochannels $40_1$, $40_2$ and in communication with respective transverse channels $30_1$, $30_2$, $32_1$, $32_2$, more than two transport nanochannels and associated components may be used, e.g., between 2-100 on a single chip, for example.

Introducing Long Genomic DNA Molecules to the Reaction Nanochannel

Figure 5:
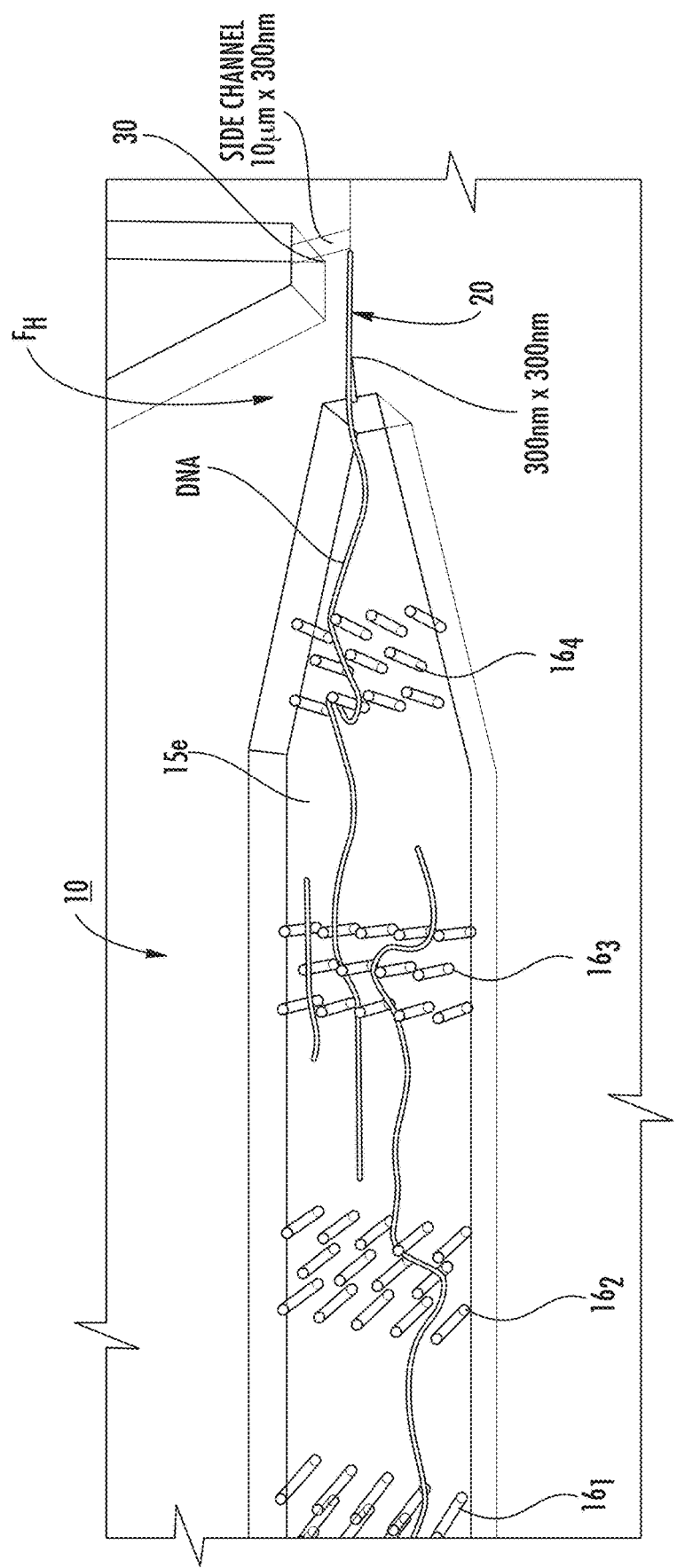
FIG. 5 is a greatly enlarged "to scale" illustration of an interface between a microfluidic channel and a nanofluidic reaction channel according to embodiments of the present invention.

In order to overcome an entropy-based energy barrier to DNA confinement, significant forces can be imposed on large DNA molecules in order to introduce them to a nanochannel. Strategies to facilitate DNA threading into the reaction nanochannel 20 without shearing include the incorporation of gradient structures and/or means of quickly reducing the field strength after threading is initiated in order to reduce stress on the molecule. As one example, using focused ion beam (FIB) milling, structures with gradually decreasing width and depth (nanofunnels) can be fabricated to serve as conduits for DNA introduction to a seamlessly interfaced nanochannel. Further descriptions of nanofunnels can be found in U.S. Provisional Application Ser. No. 61/597,364 and PCT/US2013/025078, the contents of which are hereby incorporated by reference as if recited in full herein. In another example, intersecting nanofluidic elements can be used to gain greater control of DNA transport as described in U.S. Provisional Patent Application Ser. No. 61/770,586, the contents of which are hereby incorporated by reference as if recited in full herein. FIG. 5 shows the incorporation of both of these technologies in a single device, together with a low-density array of posts 16 that encourages DNA linearization. These posts 16 can be provided as a plurality of axially spaced apart array segments or groups of posts $16_1$-$16_4$, although more or fewer segments of the same or different post array size and/or configuration can be used to partially occlude the travel path and force the DNA to travel between adjacent posts. The axial distance or spacing between post segments can be between 20-200 µm, typically about 100 µm. The length of the high-field section $F_H$ of the nanochannel 20 shown in FIG. 5 determines the force on the molecule and is relatively short to prevent undue stress on the DNA. Similarly, the distance between the last row of posts and the nanochannel entrance is great enough that the initial threading of DNA can occur without pulling the DNA taut. Loading the full DNA molecule occurs at a low velocity so that the trailing end of the molecule has sufficient time to disengage diffusively from any post entanglements. The field strength should be high enough, however, to counter the diffusion and entropic recoil that favor de-threading. The microfluidic/nanofluidic interface shown in FIG. 5 is merely one example of many structures that can be engineered for the controlled introduction of DNA to the reaction nanochannel.

Restriction Fragmentation and Fragment Sizing

Figure 6A:
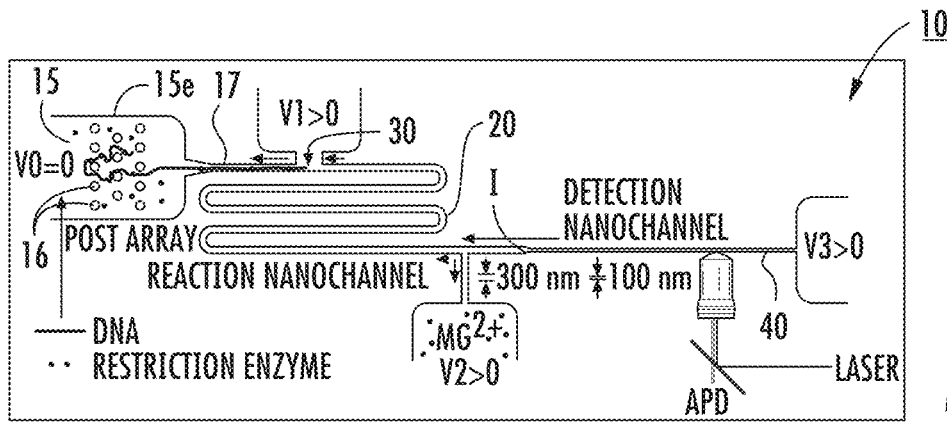
FIGS. 6A-6D are schematic illustrations of a fluidic analysis device with exemplary voltage and operational sequences according to embodiments of the present invention.
Figure 6B:
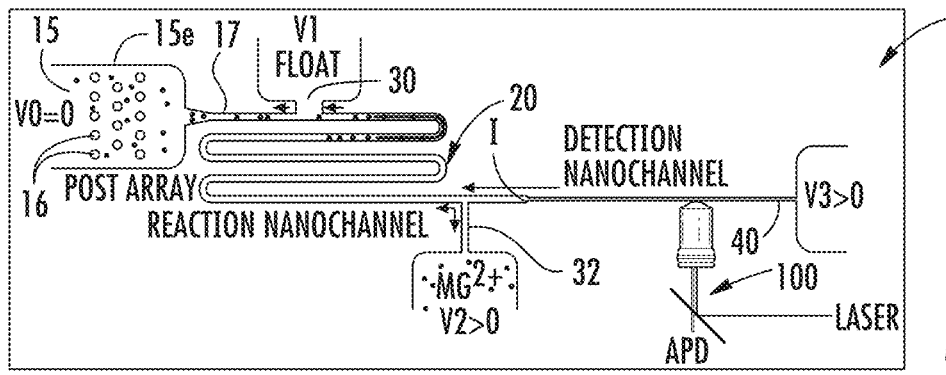
Figure 6C:
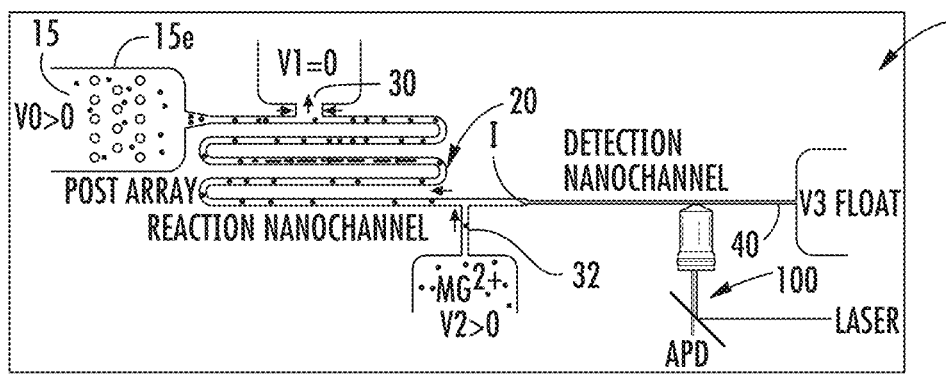
Figure 6D:
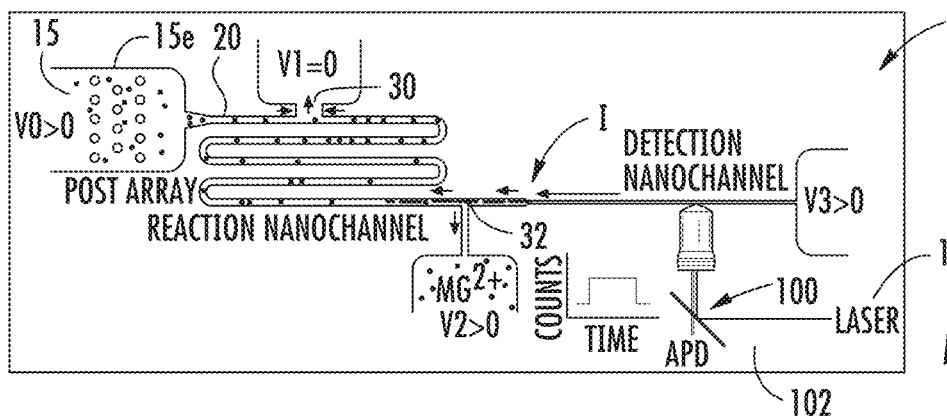
Figure 6E:
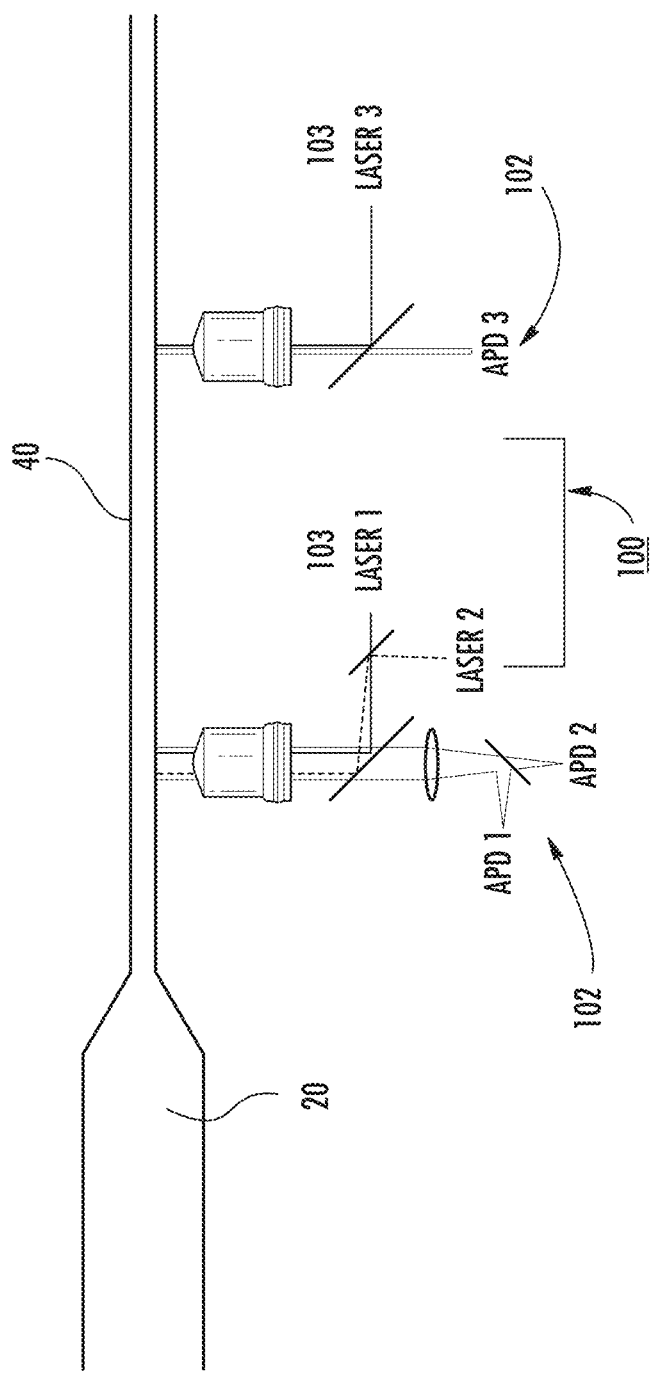
FIG. 6E is an enlarged view of the detection nanochannel with a multiple point detection circuit (rather than the single point circuit of FIG. 6D) according to embodiments of the present invention.

FIGS. 6A-6E show exemplary analysis steps conducted in the device's 10 nanofluidic channels 20, 30, 32, 40 that lead to the generation of an ordered restriction map, beginning with the threading and loading of genomic DNA described above (FIGS. 6A-6B). This is followed by the restriction digestion of the extended DNA molecule into fragments (FIG. 6C). The restriction endonuclease enzymes that digest the DNA molecule are contained in the bottom microchannel interfaced to the second transverse channel 32 in FIG. 6C (labeled by way of example only as "$Mg^{2+}$") and can also be introduced with the DNA through the entrance to the reaction nanochannel shown on the left hand side of FIG. 6C. Restriction endonucleases that require a cofactor (e.g., $Mg^{2+}$ ions) can be used to ensure that DNA fragmentation occurs only with equilibrated DNA molecules that are fully confined in the reaction nanochannel. This is accomplished by the controlled introduction of the cofactor at the appropriate time to affect restriction digestion, most easily by the application of appropriate voltages in the four channel inlets V0, V1, V2, V3 shown in FIGS. 6A-6E and 7A-7E. The polarity and magnitude of the electric fields in each of the channels during each mode of operation are indicated by arrows in FIGS. 6A-6E. Since, in this example, the cofactor is a positively charged ion, it can be electrophoretically excluded from or introduced to the reaction nanochannel 20. FIG. 6D shows the injection of DNA fragments into the detection nanochannel 40 with the aid of an array of posts 16 and a nanofunnel 17. In this example, the effective diameter of the detection nanochannel 40 is smaller than that of the reaction nanochannel 20. The reaction nanochannel 20 can be between 10 and 1000 times longer and between 2 and 100 times larger in depth and/or width than the detection nanochannel 40. For example, the reaction nanochannel 20 can have a width and depth of about 300 nm while the detection nanochannel can have a smaller width and depth, e.g., a width and depth of about 100 nm. In some embodiments, the detection nanochannel 40 has a diameter that decreases in size by between 50% to 99% from that of the reaction nanochannel 20 thereby resulting in an increase in transport velocity as each fragment reaches the intersection and the separation of each neighboring fragment.

As a result of this channel constriction, the electric field in the detection nanochannel 40 is greater than that in the reaction nanochannel 20 and DNA restriction fragments are rapidly pulled into the detection nanochannel when they arrive at the intersection. There is an inter-fragment period of time before the next fragment migrates to the intersection and is pulled into the detection nanochannel 40. As the fragments translocate through the detection nanochannel 40, they are detected downstream and the signal duration or integrated intensity is analyzed to determine the fragment size. In FIG. 6A-6D, this is accomplished by a circuit 100 for detecting the fluorescence of stained DNA fragments passing through a focused laser spot using an avalanche photodiode 102 (FIG. 6D) or multiple point detection (FIG. 6E) using, for example, two lasers 103 through a single objective lens (Laser 1 and Laser 2) or using additional objective lenses (Laser 3). Detection can also be achieved using a circuit 100' for fluorescence imaging.

In FIGS. 7A-7E, electrical single point (FIG. 7D) and multiple point (FIG. 7E) detection is illustrated (e.g., using an opposed pair of electrodes integrated with the detection nanochannel and an ammeter 101 to detect fragment-induced changes in conductance).

Figure 6F:
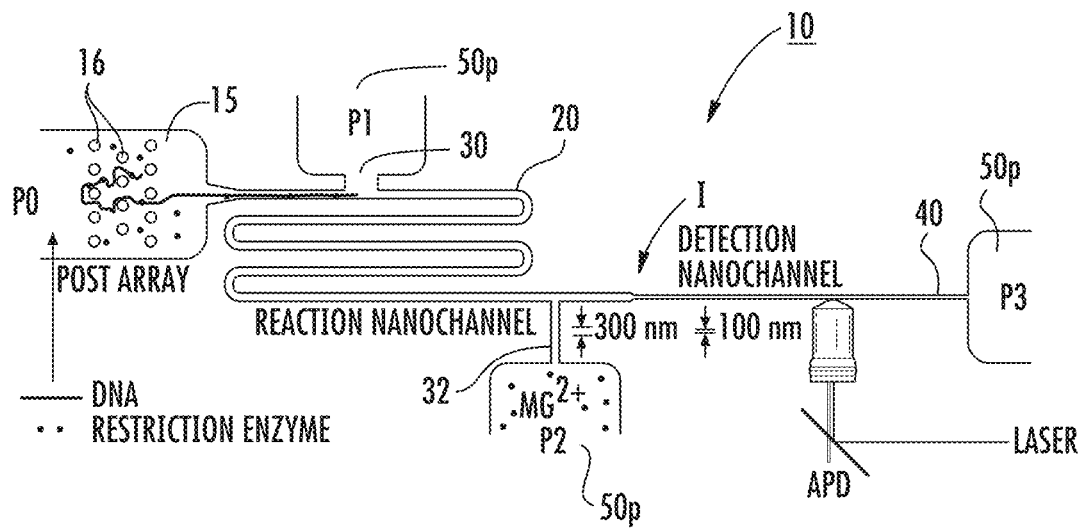
FIG. 6F is a schematic illustration of an analysis device similar to the device shown in FIGS. 6A-6E that employs pressure transport systems instead of voltage drive systems according to alternate embodiments of the present invention.
Figure 6G:
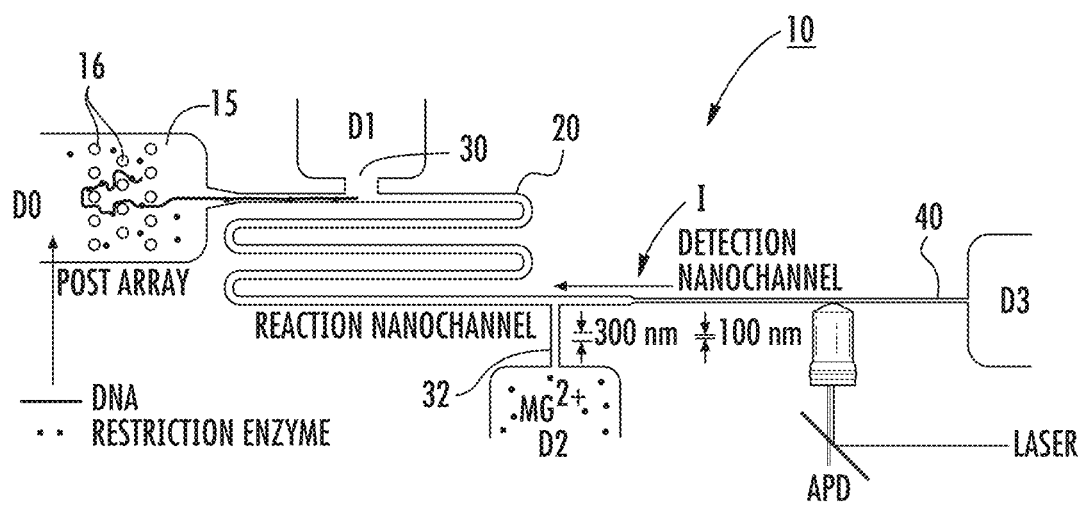
FIG. 6G is a schematic illustration of an analysis device similar to the devices shown in FIGS. 6A-6F that schematically illustrates the use of any suitable drive ("D") transport system or combinations of drive transport systems according to embodiments of the present invention.
Figure 7A:
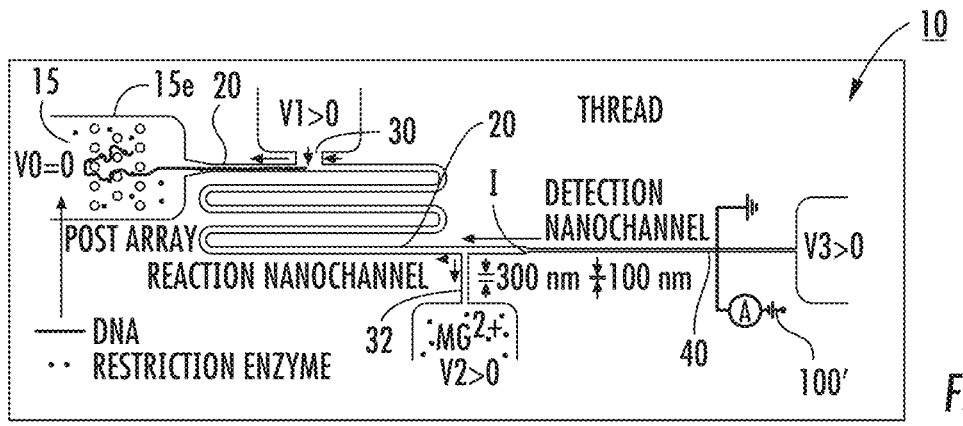
FIG. 7A-7D are schematic illustrations of a fluidic analysis device with exemplary voltage and operational sequences similar to FIGS. 6A-6D, but with an alternate detection circuit according to embodiments of the present invention.
Figure 7B:
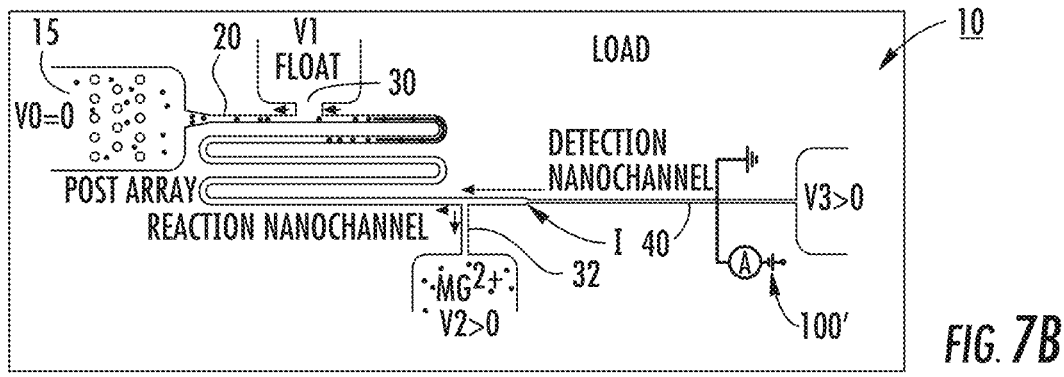
Figure 7C:
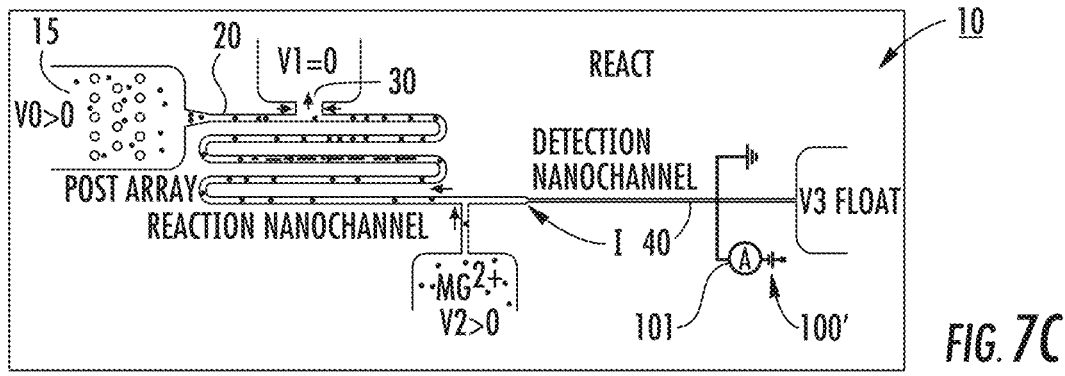
Figure 7D:
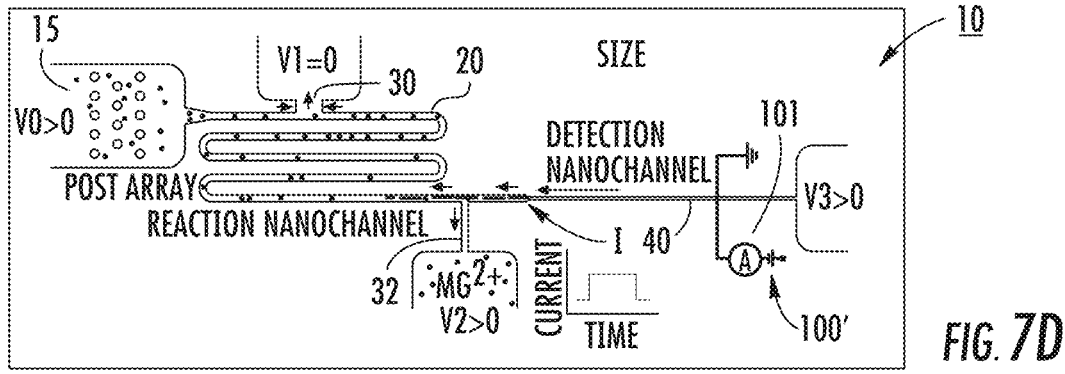
Figure 7E:
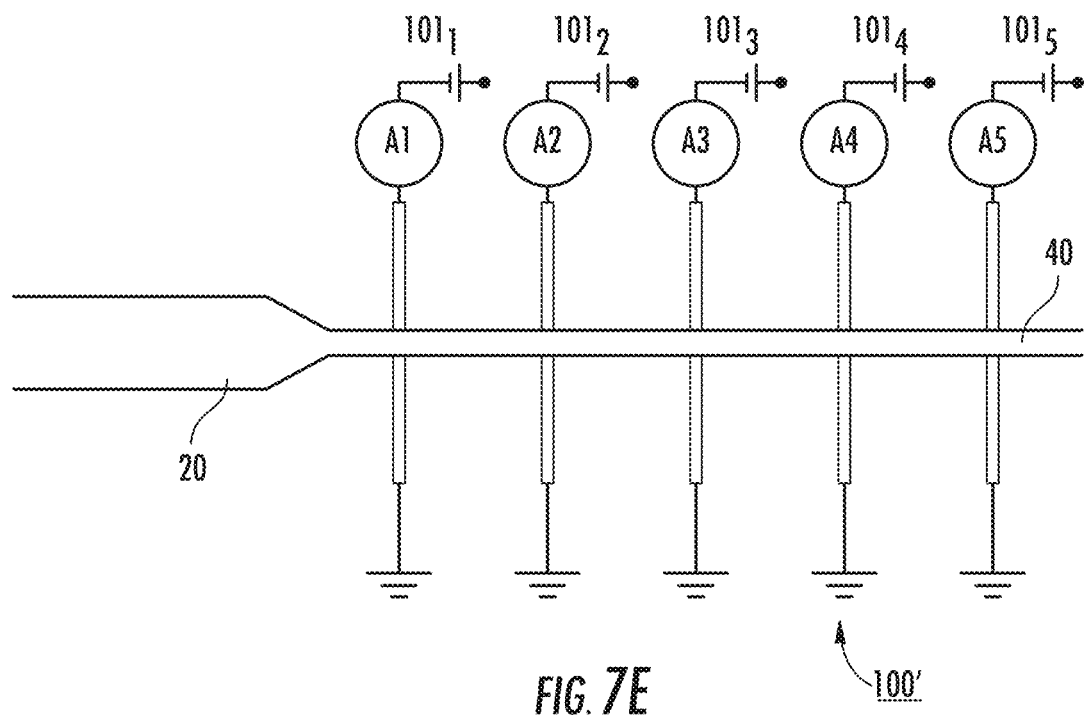
FIG. 7E is an enlarged view of the detection nanochannel with a multiple point detection circuit (rather than the single point circuit of FIG. 7D) according to embodiments of the present invention.

FIG. 6F illustrates the device 10 can be configured to operate using a pressure driven transport system of pressure/vacuum 50p via reservoirs 50 to cause the DNA molecule and fragments to thread, load and/or transport according to alternate embodiments of the present invention. The device can include conduits or tubes that connect to the pressure sources and allow automated operation along the lines noted for the electrokinetic or voltage systems. The operation of the device shown in FIG. 7A and as shown for figures illustrating other embodiments can also be operated with a pressure or other transport system. Thus, the device 10 can operate with different transport drive systems "D" or combinations of different transport drive systems as shown in FIG. 6G, such as at least one of electrokinetic, pressure, or centripetal forces that can be applied to cause transport of genomic DNA and fragments thereof through the reaction nanochannel into the detection nanochannel.

The interface between the reaction nanochannel and detection nanochannel shown in FIGS. 6A-6E and 7A-7E should also be considered one example of a class of structures where an abrupt change in the forces driving fragment transport results in fragment spatial and/or temporal resolution.

The reaction nanochannel 20 shown in FIGS. 6A-6D and 7A-7D is illustrated as having a serpentine shape with multiple parallel legs connected by "U" shaped segments. However, other nanochannel shapes can be used including straight lengths for shorter channels typically between about 500 μm to 2 cm. The serpentine shape may be particularly suitable for longer channels on a monolithic chip.

Figure 8:
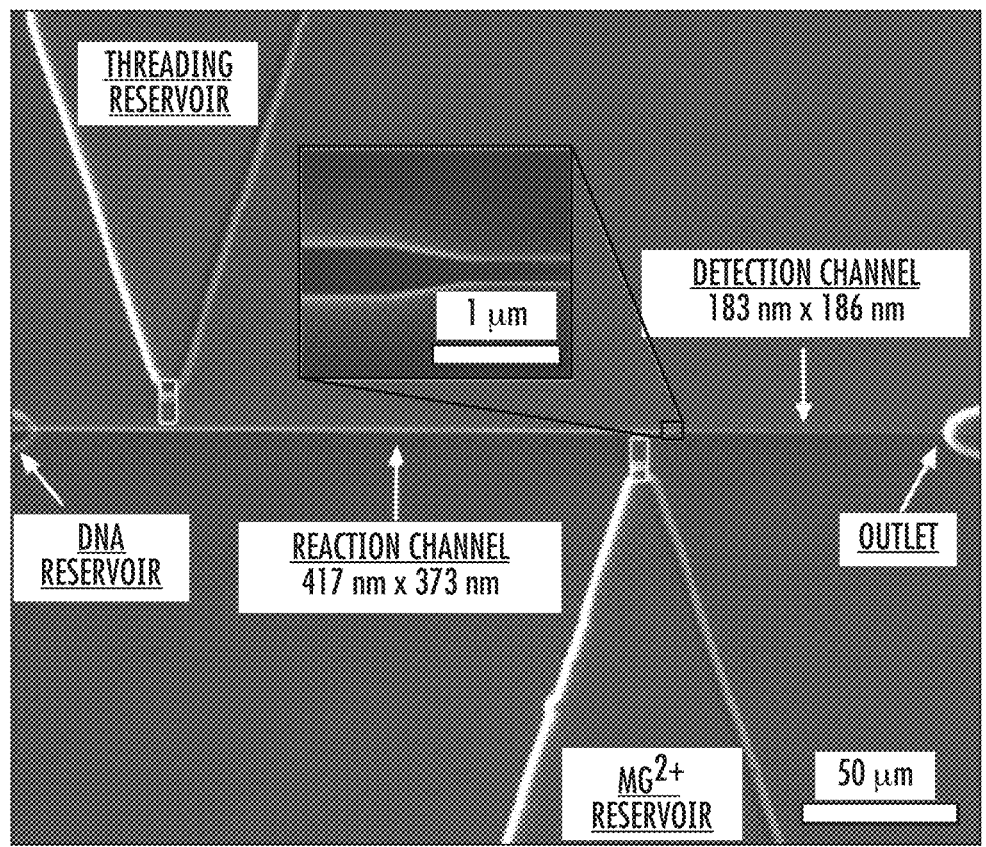
FIG. 8 is an image of a prototype fluidic device fabricated using FIB milling illustrating the fluidic structures (the enlarged insert is of the intersection between the reaction and detection nanochannels according to embodiments of the present invention.

The elements of restriction digestion, fragment resolution through injection into a detection nanochannel, and fragment sizing illustrated in FIGS. 6C-6D have been demonstrated on prototype devices (FIG. 8). These prototype devices were fabricated using focused ion beam milling and have relatively short reaction nanochannels suitable for analysis of viral or bacterial chromosomal DNA.

An advantage of an integrated nanofluidic network over nanochannels with a single input and a single output is the ability to control fluid flows using voltages at a variety of locations. In the digestion of DNA with restriction endonucleases, it can be important to control the concentration and location of the cofactor (e.g., $Mg^{2+}$ ions) to ensure digestion of the confined DNA while preventing the digestion of DNA yet to be introduced to the reaction nanochannel. In order to demonstrate this capability, a $Mg^{2+}$ sensitive dye (Magnesium Green) in electrophoresis buffer was introduced to the nanofluidic reaction and detection channels of a prototype device. Buffer with magnesium chloride (10 mM) was added to the bottom channel, as indicated in FIG. 9. The "magnesium gate" was switched between closed and open states by applying a small negative or positive voltage to the $Mg^{2+}$ reservoir, respectively, while the reaction nanochannel was held at ground. Fluorescence images were collected using a 2-s exposure with the magnesium gate closed followed by an image when the gate was opened. The intensity of the Magnesium Green increased as $Mg^{2+}$ ions migrated down the reaction nanochannel. FIG. 9B shows the increase in fluorescence during the experiment. This panel was generated by subtracting an initial frame of the recorded series (collected when the magnesium gate was closed) from the final frame with the gate open. To ensure that the increase in fluorescence was not due to concentration polarization of the dye—a phenomenon observed in nanofluidic experiments—a control experiment was conducted in which the buffer in the bottom channel was free of $Mg^{2+}$ ions. FIG. 9C shows that only a slight change in the fluorescence intensity was observed when the voltages were switched to the "open" condition. It was also possible to direct the $Mg^{2+}$ flow into the top "threading reservoir" at the other end of the reaction channel through the first transverse channel 30, preventing its introduction to the microchannel that serves as the source DNA reservoir in mapping experiments.

The digestion of DNA molecules with a restriction endonuclease in the reaction nanochannel of a prototype device has also been demonstrated. Lambda phage DNA (λ-DNA) was stained with the intercalating dye YOYO-1 (5:1 base pairs:dye molecule) in a buffer suitable for digestion using the restriction endonuclease HindIII The buffer also contained EDTA (2 mM) to sequester any $Mg^{2+}$ that might poison the DNA-containing microchannels and mercaptoethanol (4% by volume) as a radical scavenger. HindIII was then added to the DNA solution and this solution loaded into the DNA reservoir accessing the reaction nanochannel entrance. A second solution containing the reaction buffer without EDTA but with 10 mM magnesium chloride, 4% mercaptoethanol, and HindIII was added to the $Mg^{2+}$ reservoir. The remaining reservoirs (labeled "Threading" and "Outlet" in FIG. 8) were filled with buffer containing 4% mercaptoethanol (i.e., no $Mg^{2+}$, EDTA, or HindIII). Platinum electrodes were immersed in the reservoirs, enabling independent control of the voltages at the four inlets seen in FIG. 8. DNA molecules were introduced to the reaction nanochannel using a high field strength while the $Mg^{2+}$ voltage gate was closed. When a λ-DNA molecule entered the microscope's field of view, the voltages were switched to lower values so that DNA migration slowed and the $Mg^{2+}$ voltage gate was opened, driving $Mg^{2+}$ ions past the DNA molecule. After a few seconds, the voltages were adjusted so that the field strength in the reaction nanochannel was approximately zero. Images were acquired every 200 ms. After an initial imaging period of 10-15 s, the shutter of the fluorescence excitation source was closed to ensure that no photo-induced fragmentation occurred. After ~1 min of reaction, the shutter was opened to determine the extent of digestion. FIG. 10 shows a representative series of frames indicating the digestion of λ-DNA after a 1.5 min exposure to $Mg^{2+}$. In this case, three fragments were observed, indicating the partial digestion of the DNA molecule by HindIII.

Figure 11:
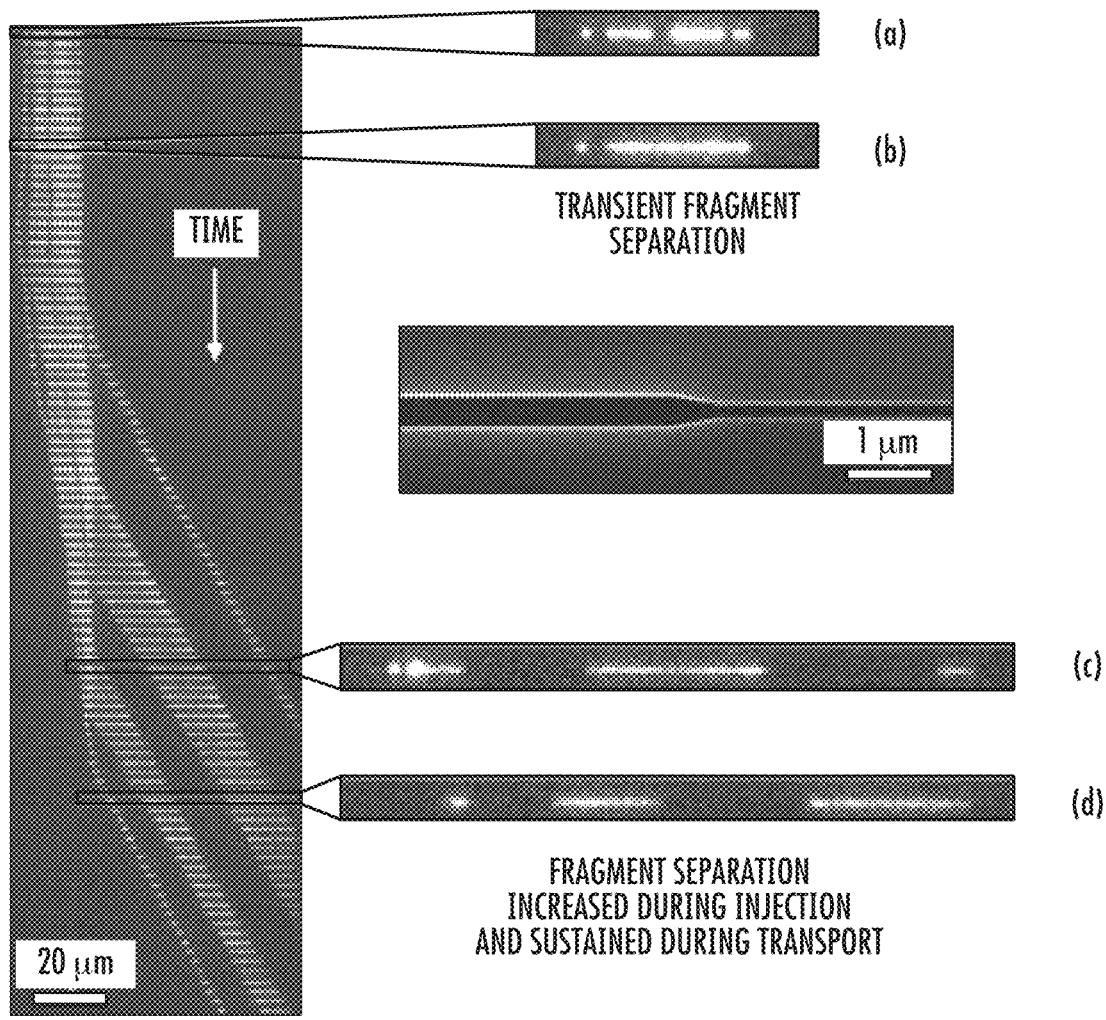
FIG. 11 is an image of a series of frames showing a fluorescently stained T4-phage DNA molecule fragmented in a 400 nm by 400 nm reaction nanochannel and injected into a 200 nm by 200 nm detection channels where the fragments are spatially well resolved during transport (lower two enlarged frames c and d) The middle inset shows an SEM image of the interface between the reaction and detection nanochannel segments. The arrow indicates time.

The resolution of DNA fragments from their neighbors in space and time through their ordered injection into a detection nanochannel has also been demonstrated in a prototype device. Fluorescently stained T4-phage DNA molecules were injected into a nanochannel with dimensions (width× depth) that were reduced from 400 nm×400 nm to 200 nm×200 nm. Given the equivalent length of the two segments, this corresponded to a four-fold increase in the electric field in the smaller nanochannel. FIG. 11 shows the diffusion of multiple fragments of a single phage molecule in the larger reaction nanochannel. (For this relatively small DNA molecule, the fragments can be resolved over the observation period represented in the figure. However, resolution of multiple large restriction fragments over larger fields of view would require extended observation periods and be subject to greater uncertainties.) This observation period was followed by the injection of fragments into the detection channel. This dynamic process effectively resulted in the full resolution of each fragment from its neighbors.

Generation of Genome Level Restriction Maps

Figure 12:
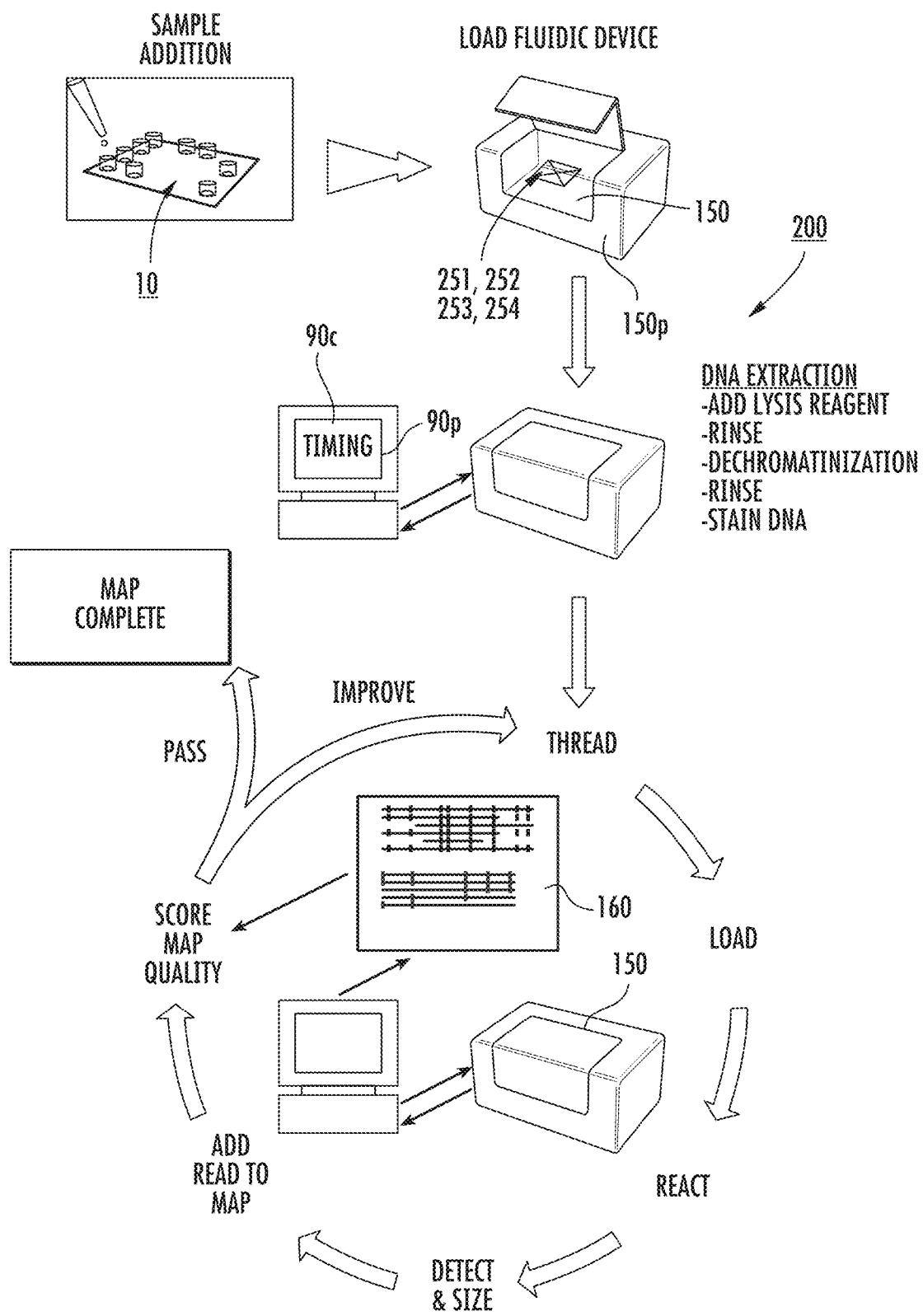
FIG. 12 is a schematic illustration of a system for restriction mapping of chromosomal DNA according to embodiments of the present invention.

FIG. 12 shows a system 200 providing an example of how the various device operations could be conducted using a bench-top apparatus 150 with computer control 90 that can serially or concurrently test a low-cost, single-use device(s) 10. Typically, after a sample of whole cells is introduced to the device 10, it is inserted into the apparatus 150. However, the device 10 may be loaded with cells after being placed in the apparatus 150. A timed program can be initiated in which reagents are flowed past the cells to achieve DNA extraction and staining in the device 10. A predefined voltage program 90p is initiated to thread the first piece of chromosomal DNA. The presence of threaded DNA (detected optically or electrically) triggers a change in the voltage program in order to fully load the DNA molecule into the reaction nanochannel 20. When this has been achieved (as determined using optical or electrical detection), the voltage program 90p is again changed to initiate the endonuclease digestion reaction. During this step, the device 10 may be heated in the apparatus 150 to enhance reaction kinetics. Following a prescribed reaction time, the voltages are automatically changed to the values used to drive the ordered injection of fragments into the detection nanochannel 40. The measured signal can be analyzed as it is collected via circuit 100, 100' (FIGS. 6D, 6E, 7D, 7E), which generates a map of the restriction sites in real time or near real time. When the detection of fragments ceases, the circuit 100, 100' can indicate to the computer 90 that the entire DNA molecule has been sampled and the "read" is complete. The voltages are changed to their "threading" values via the voltage program 90p to read the next piece of chromosomal DNA.

Figure 13A:
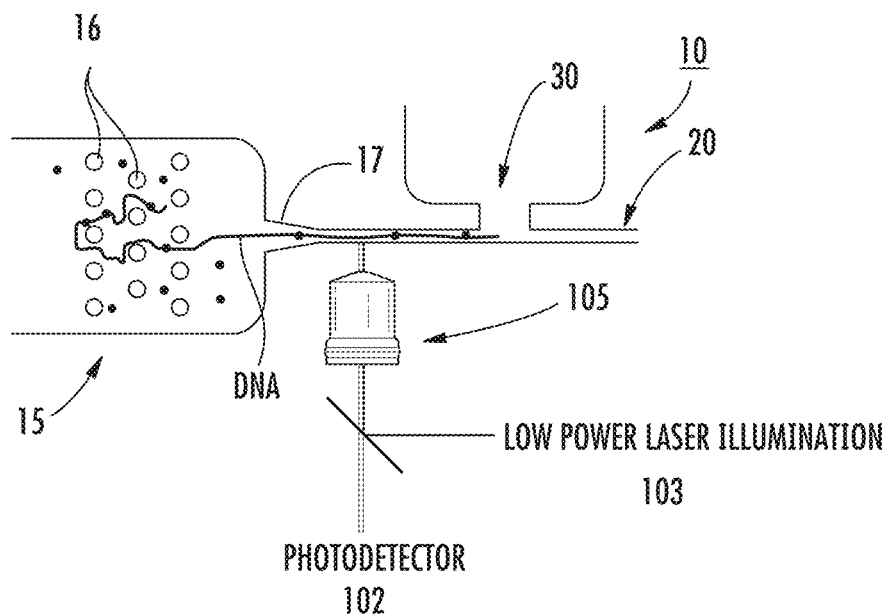
FIG. 13A is a schematic illustration of the optical detection of DNA threading into the reaction nanochannel.
Figure 13B:
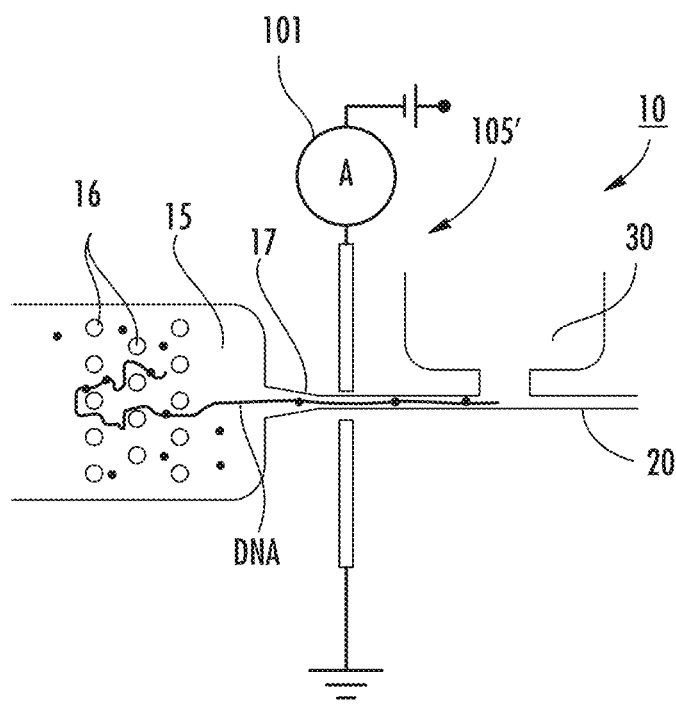
FIG. 13B is a schematic illustration of the electrical detection of DNA threading into the reaction nanochannel.
Figure 13C:
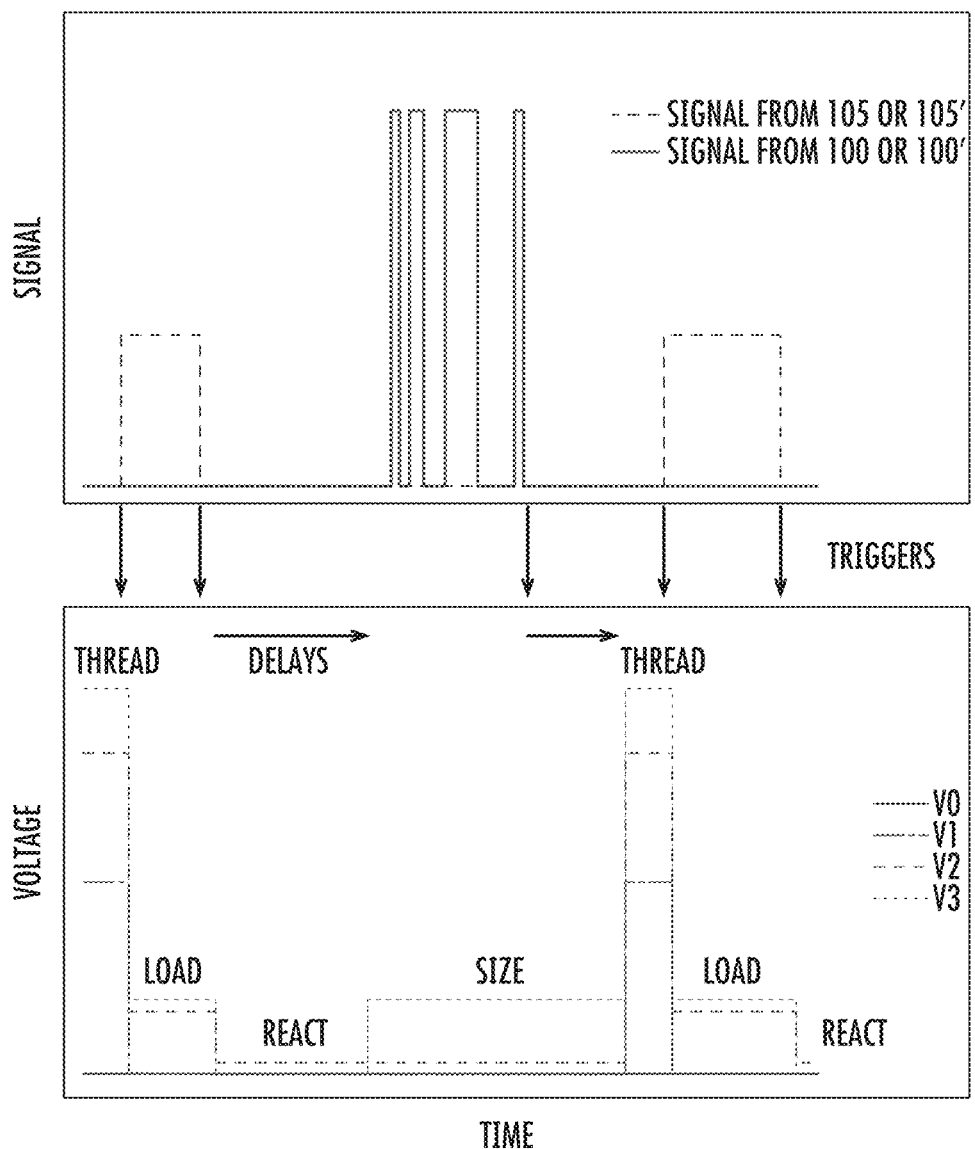
FIG. 13C is a representative voltage program for the threading, loading, reacting, and detecting of DNA molecules, with triggering initiated by the threading detection circuits and fragment detection circuits.
Figure 13D:
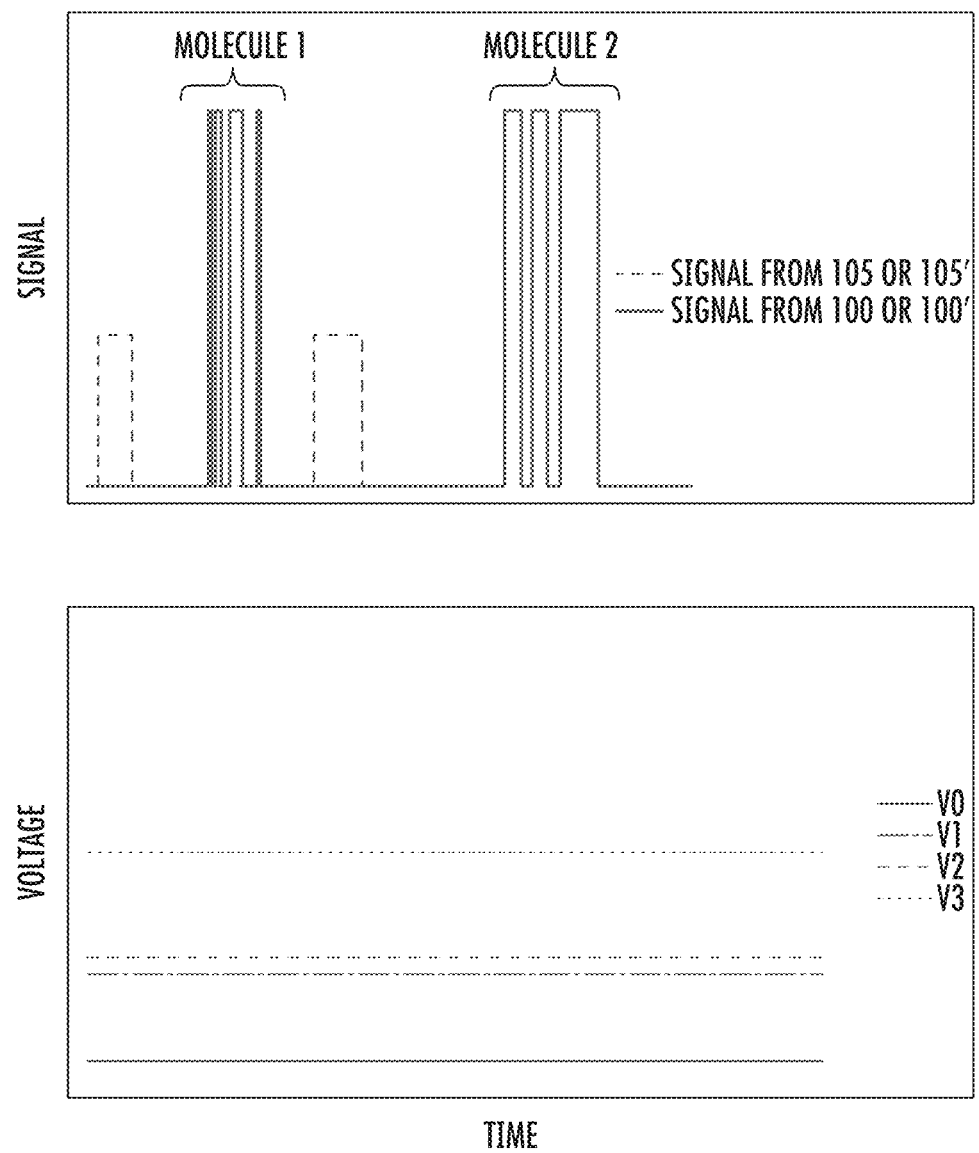
FIG. 13D illustrates a continuous mode of operation where the transport driving inputs (e.g., forces such as voltage and/or pressure) are constant.

FIGS. 13A-13B illustrate exemplary elements and circuits 105, 105' that can be used to detect the threading of a DNA molecule and FIG. 13C shows a timing/voltage control program with the triggering of the voltage program 90p directed by input from one or more control circuits such as 100, 100', 105 and/or 105'. Triggered changes in the voltage program are indicated by vertical arrows. Delays (e.g., to provide for enough time to complete the restriction digestion reaction) are indicated by horizontal arrows. The process can be repeated many times to read multiple copies of the chromosomal DNA that originated from the multiple cells initially introduced to the device. Alternatively, the device may be operated using constant voltages, pressures, or other driving forces or combinations thereof as shown in FIG. 13D. The top graph of FIG. 13D illustrates the detected signal while the bottom graph illustrates four constant input values over time corresponding to the detection time of the top graph. The term "constant" used with respect to a respective driving force input, means that the value, on average, over a defined time period, is constant to within +/−10% (e.g., a voltage and/or pressure is at +/−10% of a value over an analysis period). Stated differently, the driving force inputs are sufficiently constant to have a continuous flow versus stopped flow, but the flow rate, while being continuous, may vary with time. A series of restriction fragments are identified as originating from a single DNA molecule by their clustering with molecule separation indicated by no or a reduced detectable signal. Delays between clusters result from the sampling delay between chromosomal DNA molecules and indicate that each cluster be characterized as a unique read for a respective molecule. FIG. 13D illustrates the continuous flow detection that identifies a first cluster for Molecule 1, then a second cluster for Molecule 2, with the two adjacent clusters separated by no (or very low), e.g., detected signal time periods. At the completion of each read, that read can be computationally determined to be unique (i.e., it is the first time that chromosome has been mapped during the experimental run)

or aligned to existing map data or "reads" 160 to increase read coverage (i.e., other copies of the chromosome have been read previously in the experimental run). The long read lengths produced by this technology allow this process to be completed during the mapping experiment. Consequently, a continuously updated quality score can be produced and the analysis can be terminated after user-defined benchmarks of map coverage and quality are achieved. Alternatively, restriction mapping using additional restriction endonucleases can be initiated to generate high information content maps of various restriction sites.

FIG. 12 illustrates an automated analysis system 200 with a controlled environment housing 150 that can include a power source 150p, fluidic connections, and various chemicals for the reservoirs 50 (e.g., lysis reagents, rinse buffers, dechromatinization reagents, DNA staining solutions (where desired)). The system can control operations by injecting and withdrawing fluids through the fluidic connections and by electrically applying electrical biases, e.g., voltages, to electrodes in communication with the channels 20, 30, 32 and 40 (e.g., V0, V1, V2, V3 in FIGS. 6A-6D and FIGS. 7A-7D). The microfluidic channel 15, the fluid cross channels 30, 32 and the detection nanochannel 40 can merge into a reservoir 50 that is configured to hold a flowable substance such as a fluid (electrolyte). The reservoir fluid can comprise an electrolyte solution, e.g., a high ionic strength electrolyte solution. Examples of suitable solutions include, but are not limited to, potassium chloride solutions in concentrations from about 35 mM to about 1 M.

Referring to FIG. 12, the system 200 can include voltage inputs 251-254 to electrodes 50e (FIG. 1C) for controllably applying V0, V1, V2, V3. The system 200 can include a power source 150p (e.g., a voltage source and/or current source) that can apply the electrical bias under direction of at least one processor 90p with a desired voltage timing program or algorithm 90p with a circuit 90c that communicates with or includes the detection circuit 100, 100' (FIGS. 6D, 6E, 7D, 7E) and the threading detection circuit 105, 105' (FIGS. 13A, 13B). The system 200 can apply and control voltages V0, V1, V2, V3 at the appropriate time to thread, load, react and transport and detect the molecule under analysis or operate in a mode where the voltages are held constant as noted above with respect to FIG. 13D. Alternatively, some functions can be achieved using pressure driven flow by injecting or withdrawing solutions through fluidic connections to the device 10 according to a timing program or algorithm 90p.

FIGS. 7A-7D illustrates a detection system using circuit 100' electrical triggering of voltage change and measuring transverse conductance using an ammeter 101 and FIGS. 6A-6D illustrate a detection system 100 using an avalanche photodiode 102 and laser 103 and electrical triggering of voltage change.

FIG. 12 shows the system 200 can include a computer 90 with a circuit and/or at least one processor 90p that can obtain the analysis data for the DNA fragments in the detection nanochannel 40. The term "computer" is used broadly to include any electronic device, typically comprising at least one digital signal processor, allowing for control and communication with the circuit 100, 100' and/or device 150 to control operation. The computer can be local or remote from a site with the device 150.

The system can include an imaging system with a detector 102 and excitation source 103 (FIG. 6D) that can take a series of images of an analyte molecule in the detection channel 40. The imaging system can be any suitable imaging system. As shown, the system 100 can include an excitation light source 103 (typically for generating light that excites fluorescently labeled molecules) (which can optionally include a mirror, beam splitter, polarizer, lens, and/or other optical elements) and image generating device or detector 102 such as one or more of a camera, photomultiplier tube or photodiode. The objective/lens, where used, can reside under or over a primary surface of the device 10. The electric inputs/outputs and flow operation can reside on an opposing side of the device 10. The device 10 may also be flipped to operate on its side (with the flat primary surfaces being upright or angled) rather than substantially horizontal.

Figure 14:
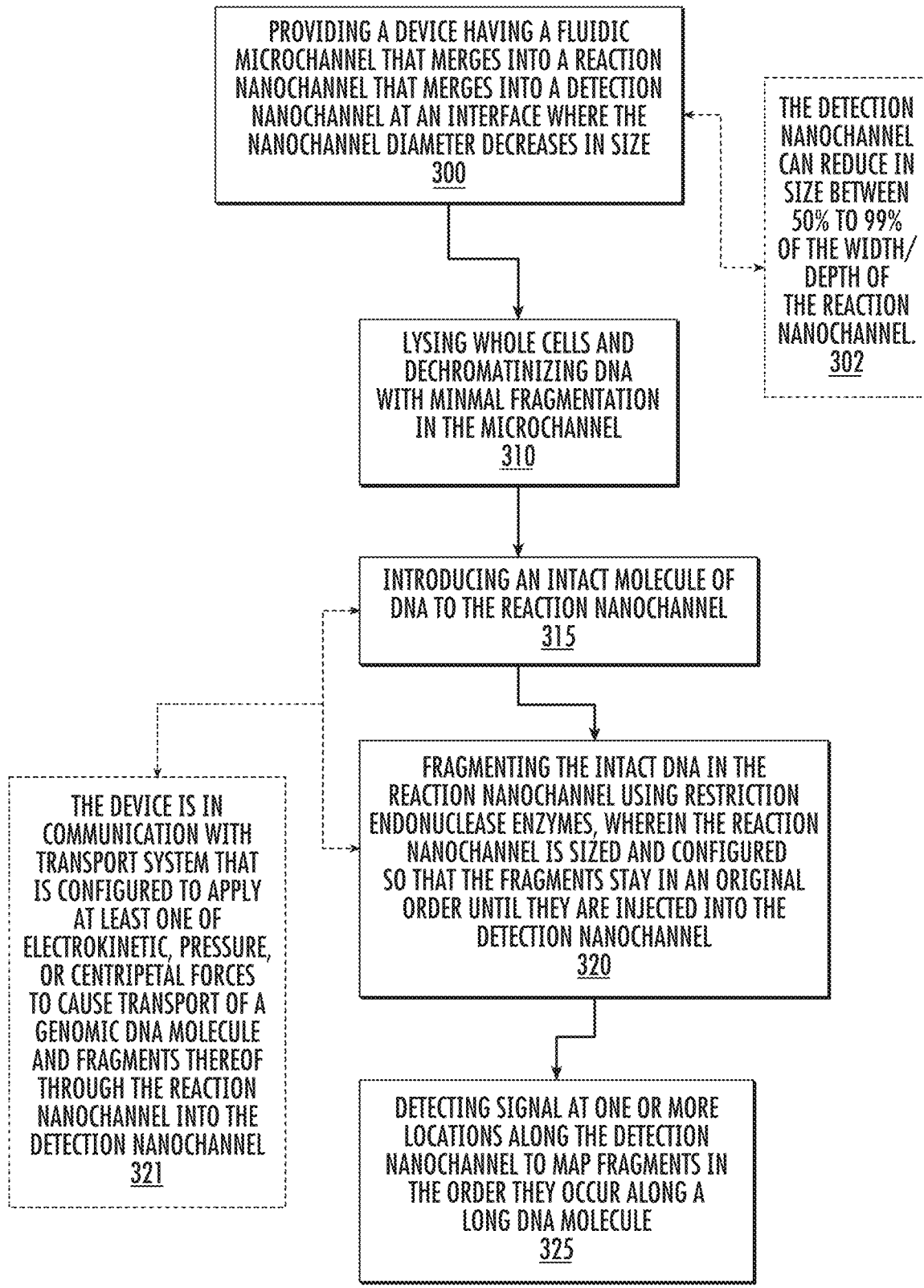
FIG. 14 is a flow chart of exemplary operations that can be carried out to map DNA fragments according to embodiments of the present invention.

FIG. 14 illustrates exemplary operations that can be used to provide DNA ordered restriction maps of genomic DNA extracted from whole cells according to embodiments of the present invention. A device having a fluidic microchannel that merges into reaction nanochannel that merges into a detection nanochannel at an interface where the nanochannel diameter decreases in size is provided (block 300). Optionally, the size reduction can be between 50% to 99% from the size of the reaction nanochannel (block 302). Whole cells can be lysed and dechromatinized to produce DNA with minimal fragmentation in the microchannel (block 310). Then an intact molecule of DNA can be introduced to the reaction nanochannel (block 315). Then the intact DNA can be fragmented in the reaction nanochannel using restriction endonuclease enzymes. The reaction nanochannel is sized and configured so that the fragments stay in an original order until they are injected into the detection nanochannel (block 320). Signal at one or more locations along the detection nanochannel can be detected to map fragments in the order they occur along a long DNA molecule (block 325).

The device can be used with a transport system that is in communication with the device, so that the transport system is configured to apply at least one of electrokinetic, pressure, or centripetal forces to cause transport of genomic DNA and fragments thereof through the reaction nanochannel into the detection nanochannel (block 321).

This technology allows for the controlled introduction of DNA from full chromosomes to a nanochannel, its digestion with restriction enzymes, and the ordered mapping of restriction fragments. Injection-based separation of fragments to resolve neighboring fragments can minimize the loss of resolution due to diffusion and reduce or eliminate the reliance on nanochannels having critical dimensions (width and depth) that approach or exceed the current limits of nanofabrication methods.

Advantageously, the smallest required nanochannel widths are typically about 100 nm. Devices can therefore be fabricated using a variety of routine methods in various substrates. See, e.g., Mijatovic, D.; Eijkel, J. C. T.; van den Berg, A. Technologies for nanofluidic systems: top-down vs. bottom-up—a review. *Lab Chip* 2005, 5, 492-500; Perry, J. L.; Kandlikar, S. G. Review of fabrication of nanochannels for single phase liquid flow. *Microfluid. Nanofluid.* 2006, 2, 185-193; Chantiwas, R. et al. Flexible fabrication and applications of polymer nanochannels and nanoslits. *Chem. Soc. Rev.* 2011, 40, 3677-3702; and Utko, P.; and Persson, F.; Kristensen, A.; Larson, N. B. Injection molded nanofluidic chips: Fabrication method and functional tests using single-molecule DNA experiments. *Lab Chip* 2011, 11, 303-308. The contents of which are hereby incorporated by reference as if recited in full herein. The ability to use wafer-scale processing can provide for a high impact, low cost technology.

Chromosomal DNA can be extracted from cells on chip and introduced without intermolecular entanglements to a nanochannel for restriction digestion and fragment sizing.

This ensures minimal DNA shearing, reducing the need for assembly of optical maps from many small overlapping contigs (contiguous consensus regions of DNA). If shearing as a result of on-chip handling does occur than the interrogated chromosomal DNA molecules can be greater than 0.5 million base pairs in length and more typically greater than 50 million base pairs in length. This is expected to increase throughput, reduce computational costs, and enable high coverage maps with low input material requirements.

Fragment sizes can be measured by imaging or single-point detection using the duration or integrated amplitude of the signal. DNA velocity can be length independent for these measurements, which is expected theoretically and has been verified experimentally in channels of this size. Data analysis can proceed in real time or near real-time, ensuring that data can be collected in a single run until the desired coverage and map quality are achieved. The elimination of large field-of-view image storage and analysis can reduce computational costs.

Integration of additional functionality is possible. For example, selected fragments can be sorted after detection for further analysis. DNA could be subjected both to restriction digestion and to a second assay such as a reaction with labeled methyl-CpG binding domain proteins or peptides. See, e.g., Lim, S. F.; Karpusenko, A.; Sakon, J. J.; Hook, J. A.; Lamar, T. A.; Riehn, R. DNA methylation profiling in nanochannels. *Biomicrofluidics* 2011, 5, 034106, the contents of which are hereby incorporated by reference as if recited in full herein. Two-color detection could thus provide single-molecule epigenetic analysis with sequence context.

For example, embodiments of the invention can be configured to identify fragments of interest and sort them into downstream channels for further analysis. These configurations may be of interest for a targeted analysis of epigenetic modifications in a specific region of the genome or for sequencing selected fragments of DNA, increasing discovery and diagnosis potential. FIGS. 15-21 illustrate examples of analysis configurations with onboard or remote reservoirs R and related methods. While these figures show molecular transport affected by electrokinetically driving the various components through the device, other transport forces in isolation or combination could be used as previously stated, including, for example, drive systems D comprising one or combinations of pressure, dielectrophoretic forces, centripetal forces, etc., as shown by way of example in FIGS. 6F and 6G.

Figure 15:
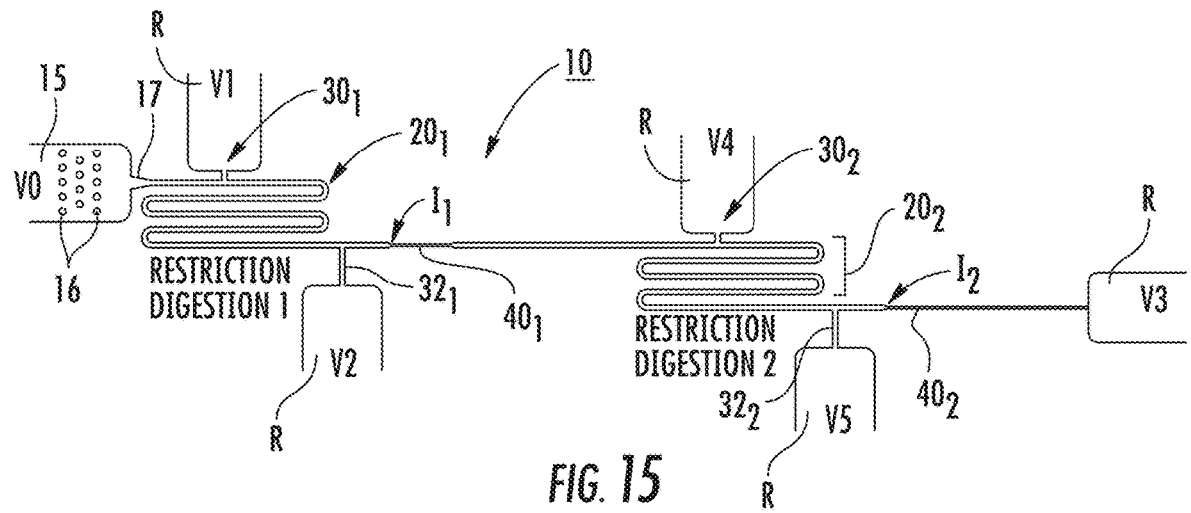
FIGS. 15, 16, 18 and 19 are schematic illustrations of devices with a plurality of serially arranged reaction nanochannels according to embodiments of the present invention.

FIG. 15 is an example of a device 10 configured to be capable of conducting two restriction digestions in series using two different reaction nanochannels $20_1$, $20_2$, one located downstream of the other. Ordered fragments from the first restriction digestion (typically all the ordered fragments) can optionally be introduced to the second reaction nanochannel $20_2$ for digestion by a second restriction enzyme. The combination of data from first and second detection channels ($40_1$ and $40_2$, respectively) provides increased or additional information about genome structure.

Figure 16:
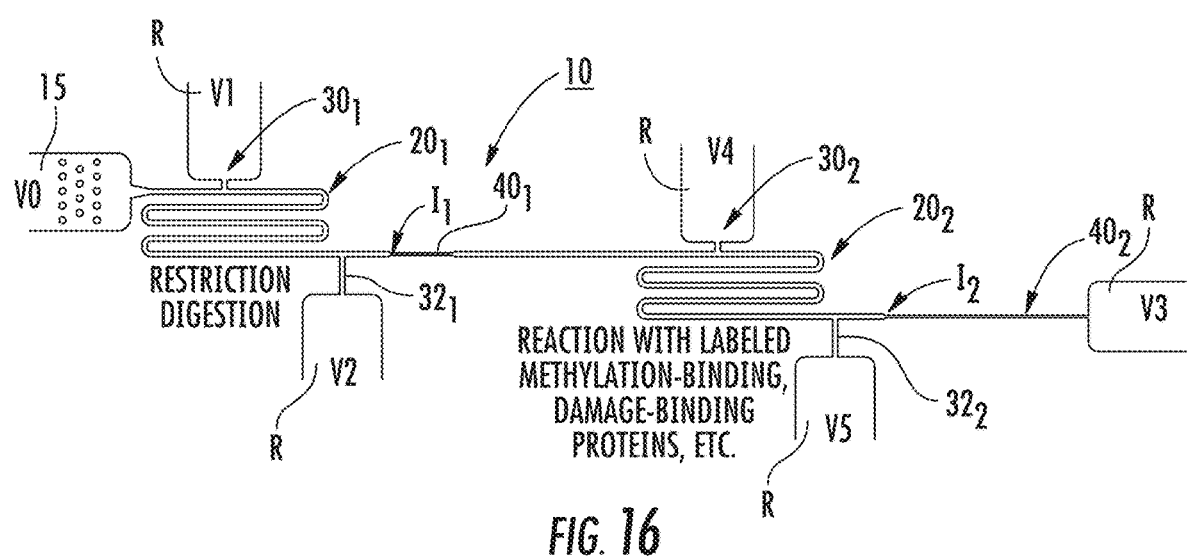

Alternatively, as shown in FIG. 16, the second reaction nanochannel $20_2$ can be configured for binding a labeled probe to the ordered fragments exiting from the first detection nanochannel $40_1$. Examples include labeled proteins that can bind to methylated regions or damaged regions of DNA, although other embodiments are possible, thereby providing additional information about a DNA sample.

In some embodiments, the devices, systems and/or methods of the present application can selectively sample fragments after they have been mapped. Because the analysis can be carried out in real time (or near real time), an observed or detected defined triggering event, e.g., detection of a defined pattern of fragments, can automatically trigger a change in the operating parameters from a primary operational mode, e.g., voltages, pressures, etc. of the transport system can have at least two defined operational modes: one for "normal" modes using less analysis time and one for fragments of more particular interest for additional analysis using the second reaction nanochannel. Thus, for example, by default, the fragments from the initial restriction digestion might be transported into an exit reservoir considered "waste" W (i.e., no additional analysis would be performed on the DNA). However, the systems and methods can be configured so that, when triggered, a series of fragments representing a region of interest in the genome can be redirected to a secondary reaction nanochannel $20_2$ and a reservoir R (also labeled as V4) can provide the material for the secondary reaction.

Figure 17:
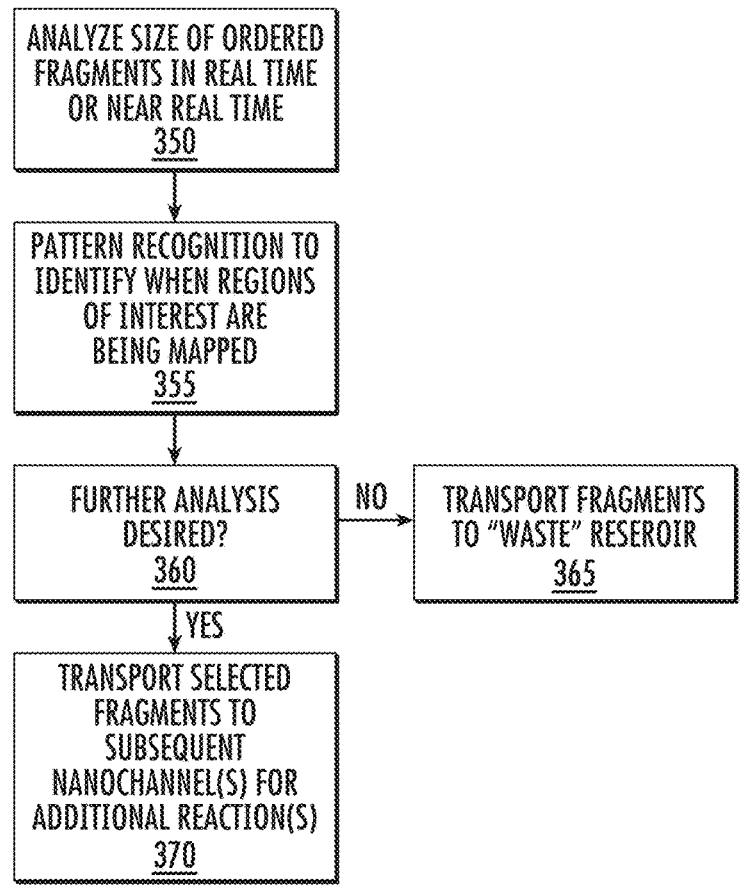
FIG. 17 is a flow chart of (typically selective) additional processing that can be carried out on fragments using the devices shown in FIGS. 15, 16, 18 and 19, for example, according to embodiments of the present invention.

FIG. 17 illustrates an exemplary triggering process. Two exemplary selective triggering systems/configurations are shown in FIGS. 18 and 19.

As shown in FIG. 17, ordered fragments can be analyzed in real time (or near real time) (block 350). Pattern recognition can be used to identify when regions of interest are being mapped (block 355). The process can have a decision node (block 360). If further analysis is desired, based on a defined trigger event or detection, the fragment(s) can be fluidically transmitted/transported to the subsequent reaction nanochannel $20_2$ (block 370). If no further analysis is desired, the fragment(s) can be transported to a waste reservoir W (block 365).

Figure 18:
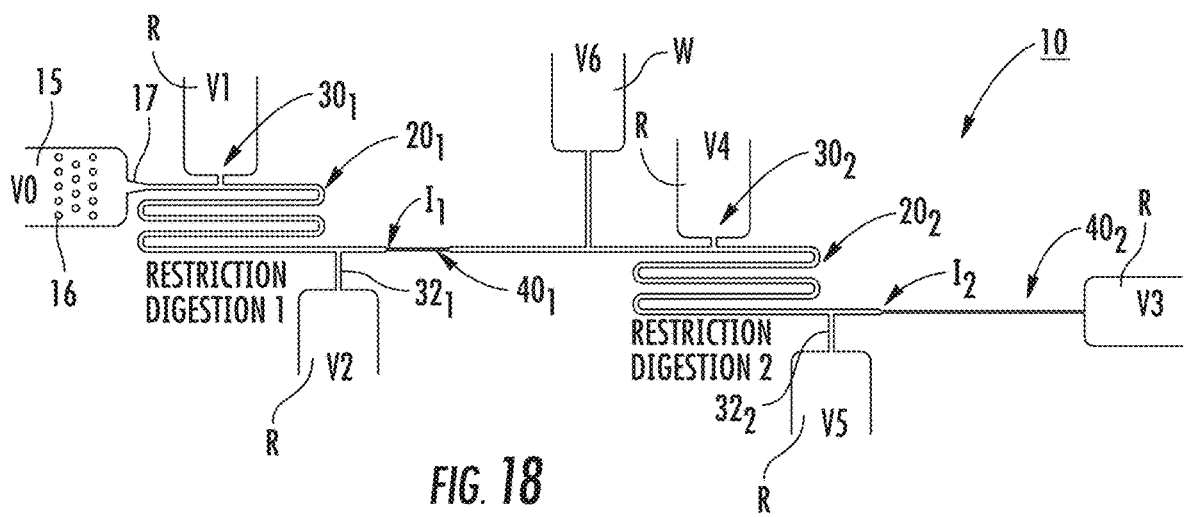

FIG. 18 shows an example of a device 10 in which most restriction fragments are transported to a waste reservoir W (also labeled "V6") while selected fragments are introduced to a second restriction digestion in the second reaction nanochannel $20_2$ by appropriately triggering the voltages (or other driving forces). The waste reservoir W can reside directly upstream of the second nanochannel $20_2$ as shown or at other locations.

Figure 19:
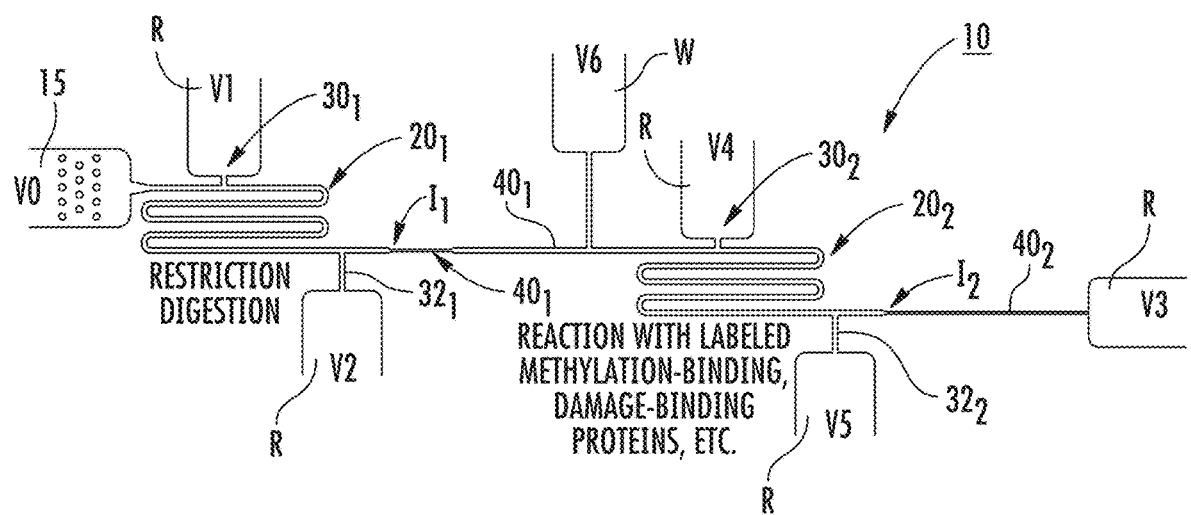

FIG. 19 is an example of a device 10 in which most restriction fragments are typically transported to a waste reservoir W (also labeled "V6") while selected fragments are introduced to a second reaction nanochannel $20_2$ by appropriately adjusting the voltages (or other driving forces) where they are bound to labeled probes such as proteins from reservoir R (also shown as V4) that can bind to methylated regions or damaged regions of DNA.

Figure 20:
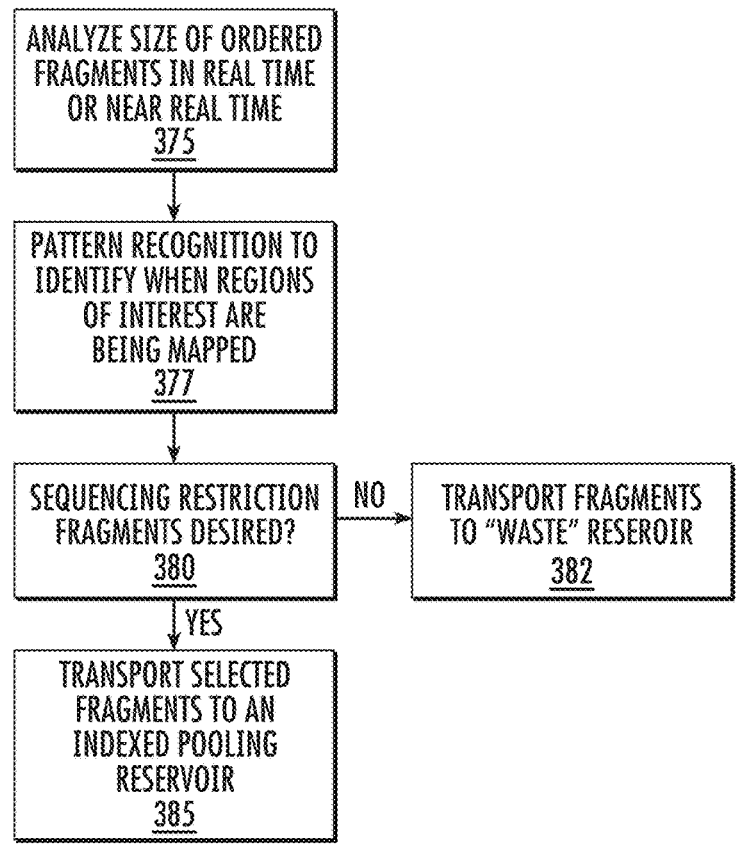
FIG. 20 is a flow chart of selective collection of restriction fragments for additional subsequent processing according to embodiments of the present invention.
Figure 21:
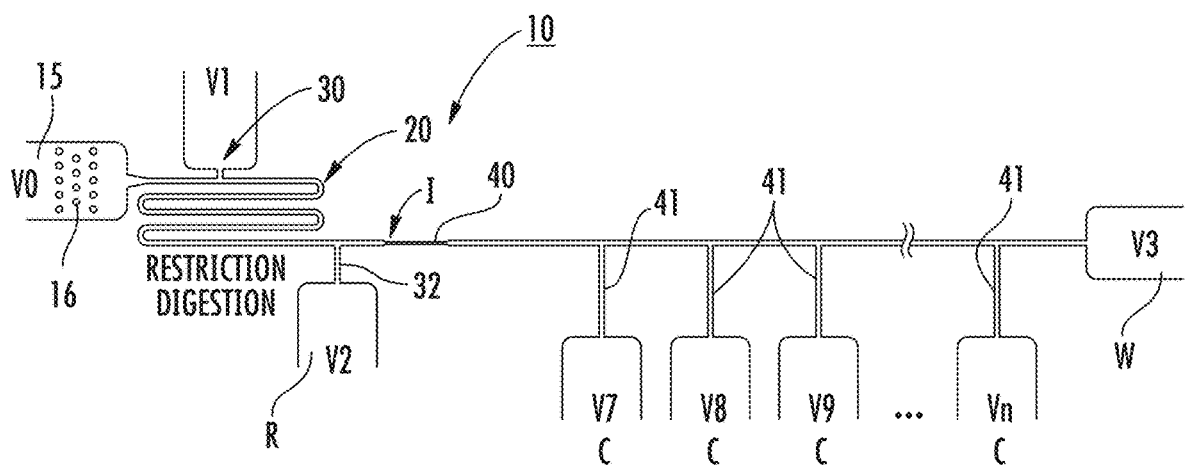
FIG. 21 is an example of a device that can be used to carry out the method shown in FIG. 20 according to embodiments of the present invention.

In addition to or alternatively to secondary reactions performed onboard the device 10 (e.g., chip), fragments from selected regions of the genome can be selectively transported to indexed reservoirs for subsequent collection and off chip analysis (e.g., sequencing). Multiple target fragments could be sorted, each to its own outlet channel. Mapping and sorting of multiple copies of the target chromosome will allow collection of sufficient material for analysis. In some embodiments, after enough material has been collected, adaptors with unique barcodes can be added to each outlet reservoir and attached to the ends of the fragments contained therein. The fragments could then be pooled (and potentially amplified), submitted for library preparation, and sequenced. FIG. 20 shows an exemplary fragment analysis, identification, and triggering process and FIG. 21 shows an exemplary device 10 in which this process can be carried out and/or implemented showing the multiple collection reservoirs "C" (labeled as V7, V8, V9 . . . Vn). The sizes of ordered fragments can be analyzed in real time (or near real time) (block 375). A defined triggering event or determination of the fragments being reviewed, e.g., pattern recognition, can identify when regions of interest are being mapped (block 377). A process decision node (block 380) can automatically assess whether sequencing restriction fragments is desired and carry out the associated transport actions to either transport fragments to the waste reservoir W (block 382) or transport the selected fragment(s) to a pooling reservoir (block 385), typically an indexed pooling reservoir for later analysis.

FIG. 21 illustrates an example of a device 10 in which restriction fragments are transported to a "waste" reservoir (labeled "V3") by default but identified fragments of interest are directed to outlet channels 41 and collected in respective collection reservoirs C (V7, V8, V9, . . . , Vn).

Embodiments of the invention have potential for high impact primarily in the areas of structural variant genotyping and de novo sequence assembly. At present, the available genetic tests that assess for elevated disease susceptibility generally identify rare, high effect single nucleotide polymorphisms (SNPs) that are typically monogenic coding errors. SNPs are not the only variants that are pathogenic, however, and genetic assessments would benefit from the inclusion of structural variants (novel insertions, deletions, duplications, inversions, and translocations). The contribution of structural variants (SVs) to disease phenotypes is less well understood than that of SNPs. Known examples include the association between SVs and schizophrenia, autism, and Crohn's disease. High-throughput, low-cost methods that can identify SVs are therefore important complements to SNP-based association studies. Current methods for identifying SVs (e.g., hybridization-based array methods and computational methods for analyzing next generation sequencing data) exhibit biases in the size and classes of variants detected, preventing global discovery. In addition to the biases inherent to each method, a large gap exists in the detection of SVs between ~300 and 10,000 base pairs. High-resolution restriction maps of chromosomal DNA provide a straightforward way to identify all classes of SVs present in an individual's genome.

In addition to their utility in detecting SVs, optical maps can also serve as scaffolds for assembly of next generation sequencing contigs. See, e.g., Lam et al, Genome mapping on nanochannel arrays for structural variation analysis and sequence assembly. *Nat. Biotech.* 2012, 30, 771-776; Zhou et al., Whole-genome shotgun optical mapping of *Rhodobacter sphaeroides* strain 2.4.1 and its use for whole-genome shotgun sequence assembly. *Genome Res.* 2003, 13, 2142-2151; and Zhou et al, A whole-genome shotgun optical map of *Yersinia pestis* strain KIM. *Appl. Environ. Microbiol.* 2002, 68, 6321-6331. The contents of which are hereby incorporated by reference as if recited in full herein.

Strategies that increase the throughput and decrease the cost of restriction site mapping can be of significant value for comparative genomics studies. Additionally, the ability of restriction mapping to span large highly repetitive regions will be valuable for assisting with difficult assemblies such as heterochromatic DNA and plant genomes.

Embodiments of the Invention can accurately map fragments in the order that they occur along a large DNA molecule. This is facilitated by the nanochannel structure where the channel diameter decreases significantly at the detection nanochannel (FIG. 11). In FIG. 11, this is shown by the series of frames on the left hand side of the image. While in some frames at the top of the series, it is apparent that there are 4 fragments, in other frames that is not obvious. Thus, one can obtain an estimate of the fragment sizes but it is not precise. Compare that to the frames in the bottom two thirds of the series where there is significant separation between fragments and greater precision in determining the fragment sizes.

Embodiments of the invention are also configured to introduce a train of fragments to the detection structure in the same order that they occur in the DNA molecule. To achieve this, an intact stretch of DNA can be introduced to the reaction nanochannel 20 and then fragmenting the DNA within that reaction nanochannel using restriction endonuclease enzymes. These enzymes fragment the DNA only at sites that have a specific sequence (e.g., the HindIII enzyme recognizes the base sequence AAGCTT and cuts the DNA between the two A's) generating a map of these sites along a molecule of DNA. The reaction nanochannel has a small enough diameter that the fragments do not intermix—they stay in the original order until they are injected into the detection nanochannel 40.

The above could be particularly suitable for introducing DNA molecules that are long, e.g., about 0.5 million base pairs long. It is contemplated that if intact DNA that is 250 million base pairs long (i.e., an entire human chromosome's worth of DNA) can be introduced to the reaction nanochannel 20, then this would greatly reduce analysis time, sample needed, and mapping errors. However, embodiments of the invention can be beneficial for other uses such as a high impact diagnostic and research tool.

While FIB milling is described for completeness and is believed to be particularly suitable for forming the nanochannels, other embodiments are directed to other forming techniques, as described above, including, for example, electron beam lithography, nanoimprint lithography, photolithography, templating or molding strategies, and other methods understood by one of ordinary skill in the art.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

That which is claimed:

1. A nanofluidic analysis system, comprising:
   a first reaction nanochannel that is from 500 μm to 10 cm long and that merges into a first detection nanochannel at an interface position therebetween where the first detection nanochannel reduces in size relative to the first reaction nanochannel;
   a microfluidic channel in communication with an ingress portion of the first reaction nanochannel;
   a first electrode in communication with the microfluidic channel;
   a first transverse fluidic channel extending from and in fluid communication with the first reaction nanochannel at a location that is spaced apart from but proximate the ingress portion of the first reaction nanochannel;
   a second electrode in communication with the first transverse fluidic channel;
   a second transverse fluidic channel extending from and in fluid communication with the first reaction nanochannel downstream, of the first transverse fluidic channel;
   a third electrode in communication with the second transverse fluidic channel;

a fourth electrode in communication with the first detection nanochannel;

a circuit configured to control operation of the first, second, third and fourth electrodes to controllably thread, load and digest DNA within the first reaction nanochannel to thereby prevent fragment disordering;

at least one electrical or optical detector in communication with the first detection nanochannel configured to spatially and temporally resolve fragment size to thereby allow an ordered restriction map of chromosomal DNA in real time or near real time; and a second reaction nanochannel that is from 500 μm to 10 cm long that resides downstream of the first reaction nanochannel and that merges into a second detection nanochannel at a second interface position therebetween where the second detection nanochannel reduces in size relative to the second reaction nanochannel.

2. The system of claim 1, wherein the microfluidic channel comprises an array of spaced apart posts configured to partially occlude the microfluidic flow path.

3. The system of claim 2, wherein the array of posts are configured as multiple segments of arrays that are axially spaced apart.

4. The system of claim 2, wherein the array of posts spans substantially across a width dimension of the microfluidic channel.

5. The system of claim 1, wherein the first and second transverse fluidic channels are fluidic nanochannels with depths from about 1 nm to about 100 nm and widths from about 20 nm to about 2000 nm, and wherein the first reaction nanochannel is from 10 to 1000 times longer and from 2 to 10 times larger in depth and/or width than the first detection nanochannel.

6. The system of claim 1, wherein the first transverse fluidic channel is either a microchannel or a nanofluidic channel or comprises segments of both, and wherein the first reaction nanochannel is from 10 to 1000 times longer than the first detection nanochannel.

7. The system of claim 1, further comprising a waste reservoir in fluid communication with the first reaction nanochannel, and wherein the circuit is further configured to selectively transport restriction fragments to either enter the waste reservoir or the second reaction nanochannel.

8. The system of claim 1, further comprising a waste reservoir and a plurality of collection reservoirs with associated outlet channels that are in fluid communication with and reside downstream of at least one of the first and second detection nanochannel, wherein the circuit is configured to control one or more of the first, second, third and fourth electrodes to selectively direct restriction fragments to either enter the waste reservoir or one of the collection reservoirs.

9. The system of claim 1, further comprising a nanofunnel residing between and connecting the first reaction nanochannel with the microfluidic inlet.

10. The system of claim 1, further comprising a plurality of reservoirs, including at least one reservoir in fluid communication with the microfluidic inlet, at least one reservoir in fluid communication with the first transverse fluidic channel, at least one reservoir in fluid communication with the second transverse fluidic channel, and at least one reservoir in fluid communication with an end of the first and/or second detection nanochannel.

11. The system of claim 10, wherein the at least one reservoir in fluid communication with the second transverse fluidic channel comprises restriction endonuclease enzymes.

12. The system of claim 1, wherein the first reaction nanochannel, the first detection nanochannel, the second reaction nanochannel, the second detection nanochannel, the first transverse fluidic channel, and the second transverse fluidic channel reside in a substrate of a planar chip.

13. The system of claim 1, further comprising:

a third transverse fluidic channel extending from and in fluid communication with the second reaction nanochannel that is spaced apart from but proximate an ingress portion of the second reaction nanochannel; and a fourth transverse fluidic channel extending from and in fluid communication with the second reaction nanochannel downstream of the third transverse fluidic channel and upstream of the second detection nanochannel.

* * * * *

UNITED STATES PATENT AND TRADEMARK OFFICE
CERTIFICATE OF CORRECTION

PATENT NO. : 10,571,428 B2
APPLICATION NO. : 15/949178
DATED : February 25, 2020
INVENTOR(S) : Ramsey et al.

Page 1 of 1

It is certified that error appears in the above-identified patent and that said Letters Patent is hereby corrected as shown below:

In the Specification

Column 4, Line 55:
Please correct "1 μmis" to read -- 1μm/s --

Column 23, Line 36:
Please correct "~300 and 10,000" to read -- ~300 and ~10,000 --

In the Claims

Column 24, Line 65, Claim 1:
Please correct "downstream, of" to read -- downstream of --

Signed and Sealed this
Twenty-third Day of June, 2020

Andrei Iancu
*Director of the United States Patent and Trademark Office*